US012605477B2

(12) United States Patent
Richardson

(10) Patent No.: US 12,605,477 B2
(45) Date of Patent: Apr. 21, 2026

(54) COMPOSITIONS AND METHODS FOR DECONTAMINATION OF SURFACES

(71) Applicant: AVIRABAN, LLC, St. Petersburg, FL (US)

(72) Inventor: Joseph J. Richardson, St. Petersburg, FL (US)

(73) Assignee: Aviraban, LLC, St. Petersburg, FL (US)

( * ) Notice: Subject to any disclaimer, the term of this patent is extended or adjusted under 35 U.S.C. 154(b) by 951 days.

(21) Appl. No.: 17/692,610

(22) Filed: Mar. 11, 2022

(65) Prior Publication Data

US 2022/0288257 A1 Sep. 15, 2022

Related U.S. Application Data

(60) Provisional application No. 63/161,111, filed on Mar. 15, 2021.

(51) Int. Cl.

| | |
|---|---|
| *A61L 2/18* | (2026.01) |
| *A01N 31/02* | (2006.01) |
| *A01N 59/16* | (2006.01) |
| *A61L 101/02* | (2006.01) |
| *A61L 101/34* | (2006.01) |
| *C08G 59/14* | (2006.01) |
| *C09D 5/00* | (2006.01) |

(Continued)

(52) U.S. Cl.
CPC ............... *A61L 2/18* (2013.01); *A01N 31/02* (2013.01); *A01N 59/16* (2013.01); *C08G 59/1438* (2013.01); *C09D 5/00* (2013.01); *C09D 7/20* (2018.01); *C09D 7/61* (2018.01);

*C09D 163/00* (2013.01); *C09D 199/00* (2013.01); *A61L 2101/02* (2020.08); *A61L 2101/34* (2020.08)

(58) Field of Classification Search
CPC .... A61L 2/18; A61L 2101/02; A61L 2101/34; A01N 31/02; A01N 59/16; C09D 7/20; C09D 7/61; C09D 199/00
See application file for complete search history.

(56) References Cited

U.S. PATENT DOCUMENTS

| | | | | |
|---|---|---|---|---|
| 4,152,170 A | * | 5/1979 | Nagase | ............... C08B 37/0018 |
| | | | | 106/205.1 |
| 10,179,114 B2 | | 1/2019 | Messersmith et al. | |

(Continued)

FOREIGN PATENT DOCUMENTS

| | | |
|---|---|---|
| CN | 108816689 A | 11/2018 |
| EP | 0953634 A1 | 11/1999 |

(Continued)

OTHER PUBLICATIONS

Matsa Group, Supply MB108 Gold dual chamber bottles with airless pump, Jan. 30, 2021.*

(Continued)

*Primary Examiner* — James M Mellott
(74) *Attorney, Agent, or Firm* — Jeffrey B. Fabian; Shumaker, Loop & Kendrick, LLP

(57) ABSTRACT

Disclosed are methods and compounds useful for forming coatings applied to porous and non-porous surfaces to make the surface antimicrobial and to protect against contaminants. The coatings are formed from phenolic compounds present in a solvent either alone or in combination with other compounds, such as metallic salts.

25 Claims, 13 Drawing Sheets

Tannic acid solution

Silver nitrate solution

Optional rinse with water

Simultaneous or sequential spray onto a mask

Antimicrobial phenolic-containing coating with tannic acid and silver

(51) Int. Cl.
*C09D 7/20* (2018.01)
*C09D 7/61* (2018.01)
*C09D 163/00* (2006.01)
*C09D 199/00* (2006.01)

(56) References Cited

U.S. PATENT DOCUMENTS

| | | | |
|---|---|---|---|
| 10,265,275 B2 | 4/2019 | Messersmith | |
| 2004/0067365 A1* | 4/2004 | Qiu | A61L 31/10 |
| | | | 428/411.1 |
| 2012/0237761 A1* | 9/2012 | Mukai | C08K 3/34 |
| | | | 428/323 |
| 2016/0002483 A1* | 1/2016 | Zhao | C09D 5/14 |
| | | | 106/18.32 |

FOREIGN PATENT DOCUMENTS

| | | |
|---|---|---|
| JP | H11180809 A | 7/1999 |
| JP | 5813269 B1 | 11/2015 |
| JP | 2005065750 A | 3/2017 |
| WO | 2009036790 A1 | 3/2009 |
| WO | WO2014197940 A1 | 12/2014 |
| WO | 2017098280 A1 | 6/2017 |

OTHER PUBLICATIONS

Tadas S. Sileika, Colorless Multifunctional Coatings Inspired by Polyphenols Found in Tea, Chocolate, and Wine, Angewandte Chemie International Edition, Aug. 22, 2013, 13 pages. vol. 52, Issue 41, John Wiley & Sons, Inc., United States of America.

Junling Guo, Boronate-Phenolic Network Capsules with Dual Response to Acidic pH and cis-Diols, Advanced Health Care Materials, Jun. 18, 2015, 4 pages, John Wiley & Sons, Inc., United States of America.

Wenjie Zhang, Cobalt-Directed Assembly of Antibodies onto Metal-Phenolic Networks for Enhanced Particle Targeting, ACS Publications, Mar. 10, 2020, 7 pages, ACS Publications, United States of America.

Yi Ju, Engineered Metal-Phenolic Capsules Show Tunable Targeted Delivery to Cancer Cells, ACS Publications, Jun. 1, 2016, 12 pages, American Chemical Society, United States of America.

Junling Guo, Engineering Multifunctional Capsules through the Assembly of Metal-Phenolic Networks, Angewandte Chemie International Edition, Apr. 2, 2014, 3 pages, vol. 53, Issue 22, John Wiley & Sons, Inc., United States of America.

Wei Luo, Engineering robust metal-phenolic network membranes for uranium extraction from seawater, Royal Society of Chemistry, Oct. 17, 2018, 6 pages, Royal Society of Chemistry, United Kingdom.

Qi-Zhi Zhong, Expanding the Toolbox of Metal-Phenolic Networks via Enzyme-Mediated Assembly, A Journal of the German Chemical Society, Nov. 24, 2019, 3 pages, John Wiley & Sons, Inc., United States of America.

Yi Ju, Improving Targeting of Metal-Phenolic Capsules by the Presence of Protein Coronas, ACS Publications, Aug. 25, 2016, 10 pages, American Chemical Society, United States of America.

Junling Guo, Influence of Ionic Strength on the Deposition of Metal-Phenolic Networks, ACS Publications, Sep. 27, 2017, 10 pages, American Chemical Society, United States of America.

Blaise L. Tardy, Lignin nano-and microparticles as template for nanostructured materials; formation of hollow metal-phenolic capsules, Green Chemistry, Feb. 20, 2018, 6 pages, Issue 6, Royal Society of Chemistry, United Kingdom.

Wenjie Zhang, Metal-dependent inhibition of amyloid fibril formation: synergistic effects of cobalt-tannic acid networks, Nanoscale, Jan. 15, 2019, 6 pages, Issue 4, Royal Society of Chemistry, United Kingdom.

Jingqu Chen, Metal-Phenolic Coatings as a Platform to Trigger Endosomal Escape of Nanoparticles, ACS Publications, Oct. 1, 2019, 11 pages, American Chemical Society, United States of America.

Dr. Shuaijun Pan, Modular Assembly of Host-Guest Metal-Phenolic Networks Using Macrocyclic Building Blocks, A Journal of the German Chemical Society, Oct. 24, 2019, 3 pages, John Wiley & Sons, Inc., United States of America.

Junling Guo, Nanoporous Metal-Phenolic Particles as Ultrasound Imaging Probes for Hydrogen Peroxide, Advanced Healthcare Materials, Sep. 1, 2015, 3 pages, John Wiley & Sons, Inc., United States of America.

Hirotaka Ejima, One-Step Assembly of Coordination Complexes for Versatile Film and Particle Engineering, Science, Jul. 12, 2013, 6 pages, vol. 341, Issue 6142, www.science.org, United States of America.

Zhixing Lin, Ordered Mesoporous Metal-Phenolic Network Particles, ACS Publications, Dec. 18, 2019, 8 pages, American Chemical Society, United States of America.

Qi-Zhi Zhong, Oxidation-Mediated Kinetic Strategies for Engineering Metal-Phenolic Networks, A Journal of the German Chemical Society, Jul. 18, 2019, 3 pages, John Wiley & Sons, Inc., United States of America.

Jiajing Zhou, Particle engineering enabled by polyphenol-mediated supramolecular networks, Nature Communications, Sep. 23, 2020, 32 pages, Nature Communications, United States of America.

Yuan Ping, pH-Responsive Capsules Engineered from Metal-Phenolic Networks for Anticancer Drug Delivery, Wiley Online Library, Jan. 3, 2015, 3 pages, John Wiley & Sons, Inc., United States of America.

Yiyuan Han, Polyphenol-Based Nanoparticles for Intracellular Protein Delivery via Competing Supramolecular Interactions, ACS Publications, Sep. 30, 2020, 7 pages, American Chemical Society, United State of America.

Yiyuan Han, Polyphenol-Mediated Assembly of Proteins for Engineering Functional Materials, A Journal of the German Chemical Society, Mar. 1, 2020, 3 pages, John Wiley & Sons, Inc., United States of America.

Jingqu Chen, Programmable Permeability of Metal-Phenolic Network Microcapsules, American Chemical Society, Aug. 4, 2020, 7 pages, American Chemical Society, United States of America.

Blaise L. Tardy, Protein Adsorption and Coordination-Based End-Tethering of Functional Polymers on Metal-Phenolic Network Films, ACS Publications, Feb. 22, 2019, 7 pages, American Chemical Society, United States of America.

Gyeongwon Yun, Self-Assembly of Nano-to Macroscopic Metal-Phenolic Materials, ACS Publications, Aug. 9, 2018, 8 pages, American Chemical Society, United States of America.

Qi-Zhi Zhong, Spray Assembly of Metal-Phenolic Networks: Formation, Growth, and Applications, ACS Publications, Sep. 21, 2018, 10 pages, American Chemical Society, United States of America.

Gyeongwon Yun, Synthesis of Metal Nanoparticles in Metal-Phenolic Networks: Catalytic and Antimicrobial Applications of Coated Textiles, Wiley Online Library, Oct. 12, 2017, 3 pages, John Wiley & Sons, Inc., United States of America.

Subin Kim, Tannic acid-functionalized HEPA filter materials for influenza virus capture, Scientific Reports, Jan. 13, 2021, 22 pages, Springer Nature Limited, United States of America.

Gyeongwon Yun, The Biomolecular Corona in 2D and Reverse: Patterning Metal-Phenolic Networks on Proteins, Lipids, Nucleic Acids, Polysaccharides, and Fingerprints, Wiley Online Library, Oct. 31, 2019, 4 pages, John Wiley & Sons, Inc., United States of America.

Dr. Gao Xiao, Thermal Transition of Bimetallic Metal-Phenolic Networks to Biomass-Derived Hierarchically Porous Nanofibers, Wiley Online Library, Feb. 22, 2018, 3 pages, John Wiley & Sons, Inc., United States of America.

Gyeongwon Yun, Tuning the Mechanical Behavior of Metal-Phenolic Networks through Building Block Composition, ACS Publications, Feb. 5, 2019, 7 pages, American Chemical Society, United States of America.

(56)             References Cited

OTHER PUBLICATIONS

European Extended Search Report for EP 22771961.4; Jan. 17, 2025; 11 pgs.

* cited by examiner

Tannic acid solution

Silver nitrate solution

Optional rinse with water

Simultaneous or sequential spray onto a mask

Antimicrobial phenolic-containing coating with tannic acid and silver

Infectious Microbes

Infectious Microbes $Ag^+$ + Tannic Acid (TA)

Textile

Ag/TA-Coated Textile

Infectious Microbes

Neutralized Microbes

Normalized Odor Compostition by Olfactometry

COMPOSITIONS AND METHODS FOR DECONTAMINATION OF SURFACES

TECHNICAL FIELD AND BACKGROUND

The present invention relates generally to compositions and uses of such compositions in depositing coatings that bind to and/or inactivate biological contaminants in air and liquid, such as microbes and pollutants, and to methods for depositing these coatings.

Antimicrobial and antipollution materials are important as individuals in medical, commercial, and everyday settings are only protected from exposure to microbes and their effects by wearing personal protective equipment ("PPE") such as gloves, masks, scrubs, and lab coats. Currently, one of the biggest challenges in PPE is that microbes can adhere to, collect on, and pass through most types of fabrics. Therefore, when the public wears masks, it is to prevent spreading viral contaminants to others, but masks do not effectively prevent spreading viral contaminants deposited from other individuals.

The complete redesign of PPE is not practical when rapid response is needed. Instead, approaches focusing on improving existing PPE should be encouraged. For example, standard surgical masks filter about 60-80% of particles smaller than 2.5 microns ($\mu m$) ($PM_{2.5}$). But higher quality N95 masks cut out more than 95% of small particles and are viewed as the gold standard for preventing infection.

What is needed are simple and affordable approaches to improving the performance of PPE such as masks that make the surfaces less likely to transmit microbes and pollution. To be practical, such approaches must fulfill objectives that include: (i) effectively binding or neutralizing microbes and pollutants; (ii) convenient to apply in manufacturing and field settings; (iii) utilization of safe precursor materials and assembly processes; (iv) being safe to use and dispose; and (v) achieving conformance and adherence to every fiber in the fabric. Surfaces other than fabric materials face similar challenges that must be met. Accordingly, it is an object of the present technology to develop mask, fabric, and surface coatings with these properties to minimize the negative impacts of microbes, such as contamination, infection, transmission, and/or odor among others.

SUMMARY

The present technology includes compositions, systems, and processes that relate to phenolic compounds used for fabric and surface coatings for antimicrobial and antipollution applications.

Phenolic compounds and coatings can be synthesized, deployed, and utilized in various ways for the coating of substrates to increase their binding to, and inactivation of, various biological contaminants and pollutants. The compositions provided herein can adhere to substrates and bind to, and/or inactivate, a wide variety of natural contaminants and microbes. Configuration, use, and operation of these compositions in relation to binding various contaminants and pollutants can involve phenolic-containing coatings that allow for strong molecular adhesion forces to physically and chemically bind the contaminants to the coated surface and to physically and chemically inactivate the contaminants by themselves and with the inclusion of antimicrobial agents.

Such phenolic-containing coatings can be deposited on porous and non-porous substrates and the composition, thickness, and density of the coatings can be tailored to optimize binding and inactivation of different contaminants.

The coatings can be cleaned with various surfactants and removed with specific chemicals or through abrasion depending on the substrate. Various methods for making phenolic-containing coatings are provided, including the making of solutions, deposition of coatings on substrates, use of the solutions and liquid dispersions of the phenolic and other components, ways of applying the coatings, and ways of capturing and inactivating contaminants using the coatings as described herein.

Coating a surface can include contacting the surface with a composition, where the composition includes a phenolic molecule by itself or with another compound. The composition can be made by combining a phenolic molecule and a solvent to form a solution, and can be optionally mixed with other compounds, solvents, and/or solutions. The solution(s) can then be applied to the surface via immersion, spraying, wiping, pouring, blotting, exhaustion, or other similar methods to deposit the coating. The deposited coating can then capture, inactivate, bind, or otherwise filter out and prevent the passage of contaminants. The coating can be made in a thickness range from 0.01 nm to about 1 mm.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

These and other features, aspects and advantages of the present invention are better understood when the following detailed description of the invention is read with reference to the accompanying Figures.

DETAILED DESCRIPTION

Figure 1A:
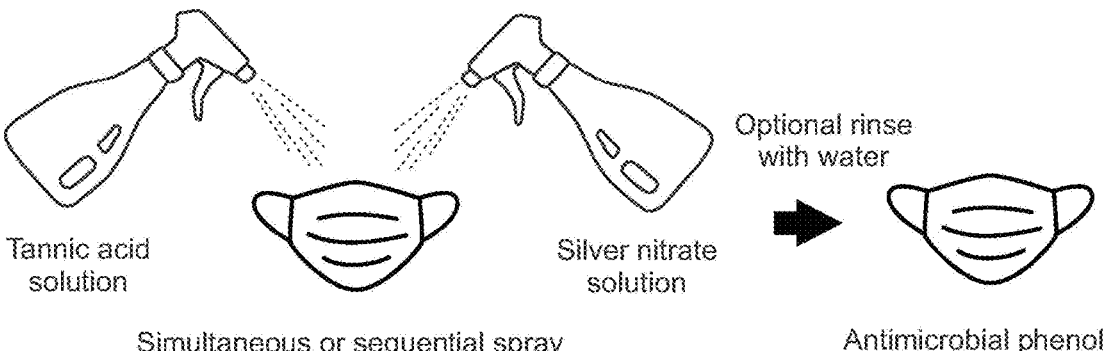
FIG. 1A illustrates a method for applying a phenolic coating of tannic acid and silver nitrate to a mask.

The present invention will now be described more fully hereinafter with reference to the accompanying drawings in which example embodiments of the invention are shown. However, the invention may be embodied in many different forms and should not be construed as limited to the representative embodiments set forth herein. The example embodiments are provided so that this disclosure will be both thorough and complete and will fully convey the scope of the invention and enable one of ordinary skill in the art to make, use, and practice the invention.

Regarding methods disclosed, the order of the steps presented is illustrative in nature, and, therefore, the order of the steps can be different in various embodiments. Words such "a" and "an" as used herein indicate "at least one" of the item is present; a plurality of such items may be present, when possible. It will be understood that relative terms are intended to encompass different orientations or sequences in addition to the orientations and sequences depicted in the drawings and described herein. Except where otherwise expressly indicated, all numerical quantities in this description are to be understood as modified by the word "about" and all geometric and spatial descriptors are to be understood as modified by the word "substantially" in describing the broadest scope of the technology.

"About" when applied to numerical values indicates that the calculation or the measurement allows some slight imprecision in the value (with some approach to exactness in the value; approximately or reasonably close to the value; nearly). Relative terminology, such as "substantially" or "about," describe the specified devices, materials, transmissions, steps, parameters, or ranges as well as those that do not materially affect the basic and novel characteristics of the claimed inventions as whole (as would be appreciated by one of ordinary skill in the art). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of". Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology provides compositions and methods for forming and utilizing phenolic-containing coatings that can be used in various ways, including use in the capture, filtration, inactivation, decontamination, and similar of biological contaminants and pollutants. The compositions provided herein can adhere to substrates and surfaces and subsequently bind to, repel, inactivate, filter, and/or decontaminate, a wide variety of natural contaminating molecules, particles, biological entities, including but not limited to bacteria, virus, prions, fungus, proteins, pollen, small molecules, and similar in gas, liquid and solid media. Configuration, use, and operation of these compositions in relation to excluding contaminants can involve phenolic-containing solutions and coatings.

Figure 2A:
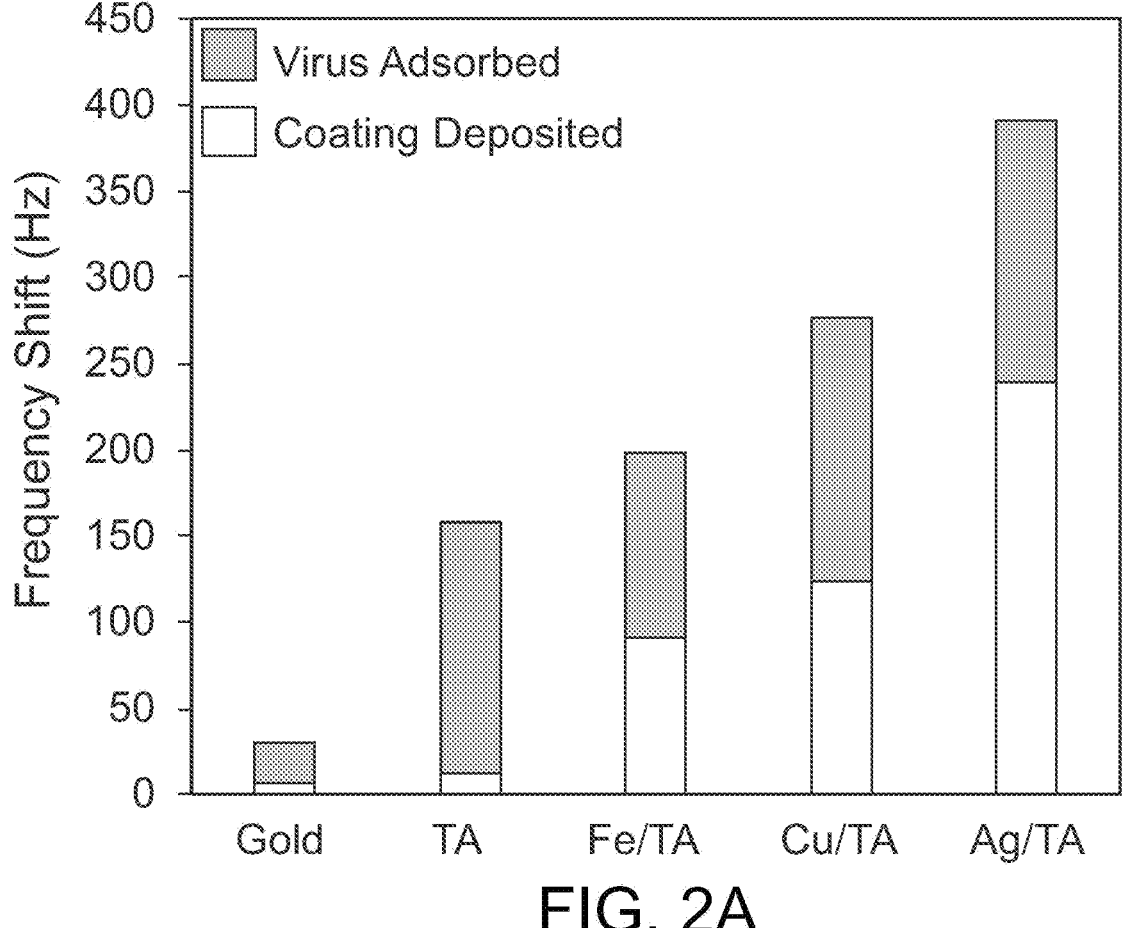
FIG. 2A illustrates experimental results for the binding affinity of phenolic coatings of different composition on gold and their binding affinity to viruses.
Figure 2B:
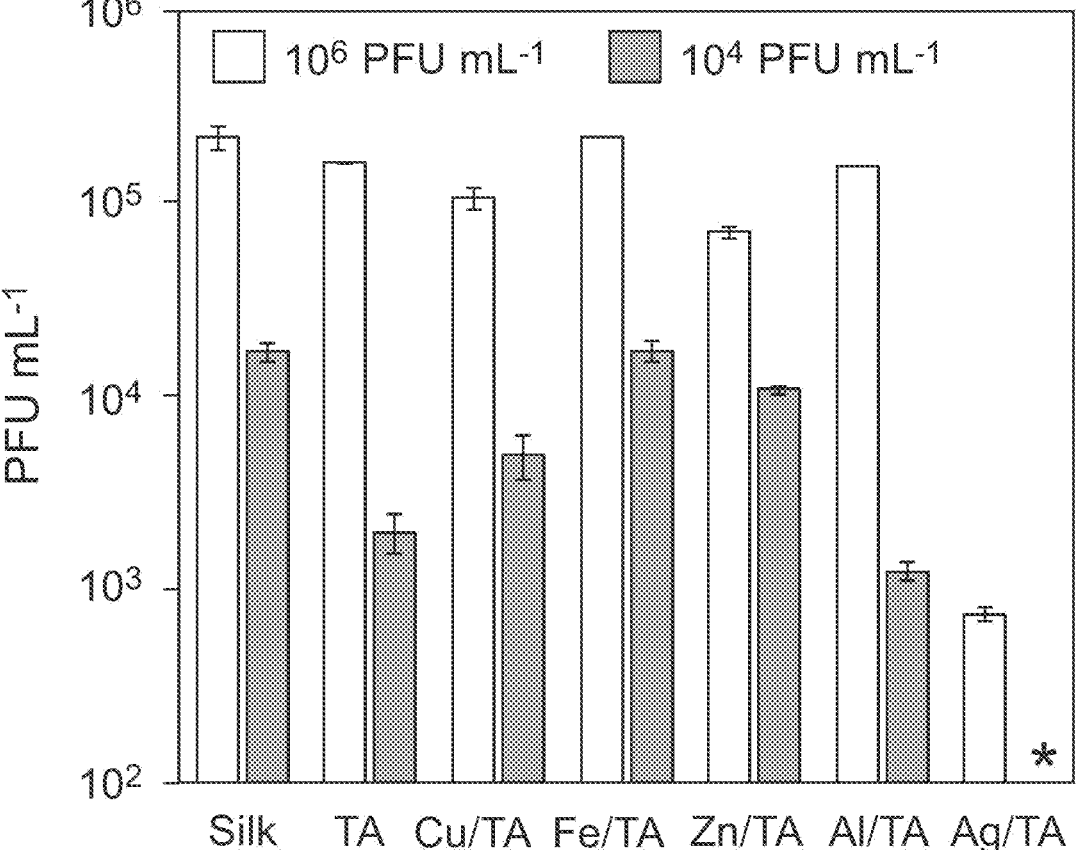
FIG. 2B illustrates experimental results for viral reduction resulting from application of various compositions on silk masks.

FIGS. 2A and 2B illustrate the effectiveness of the coatings in protecting against viruses. FIG. 2A shows experimental results for the binding affinity of phenolic coatings of different composition on gold and their binding affinity to viruses (Phi6). FIG. 2A highlights the higher binding affinity of phenolic coatings versus the bare gold and the metal-dependent nature of the virus binding. Specifically, FIG. 2A shows the frequency shift (1st overtone) and associated mass of coatings deposited using tannic acid by itself and with different metals and their subsequent ability to interact with viruses as monitored by quartz crystal micro-gravimetry.

FIG. 2B illustrates experimental results for viral reduction at different viral (Phi6) loads (plaque forming units per mL, or PFU mL$^{-1}$) resulting from application of various compositions of phenolic coatings on silk masks. These results highlight the metal-dependent performance of the phenolic coatings in terms of viral reduction. Specifically, no virus was detectable at the lowest concentration ($10^4$ PFU mL$^{-1}$) when incubated with phenolic coatings prepared with silver nitrate (Ag/TA) (marked with *), where $10^2$ PFU mL$^{-1}$ was the minimum detectable concentration of the assay.

The phenolic-containing coatings can be substantially non-porous or can be porous. Porosity can be adjusted to specifically capture contaminants of defined sizes while letting smaller materials pass through un-hindered, or for the pores to act as additional size-dependent capture sites. Porosity can be adjusted, including varying the number and size of pores by, for example, washing the coatings with various solvents and/or surfactants, using higher or lower phenol concentrations in the reaction constituents, varying the reaction conditions (e.g., temperature, volume, pressure), using different phenolic molecules, and using different additive compounds.

Additive compounds can enhance the inactivation of contaminants where, for example, antimicrobial additives such as antimicrobial metals or organic molecules can be incorporated into the coatings during deposition. The additives can also control the durability, where compounds that strongly interact with phenolics, such as iron, zirconium, or cationic polymers, will provide durability against large pH and solvent ranges. On the other hand, weakly interacting compounds, such as neutral polymers, copper, and similar components, will produce coatings that can readily be removed in a wash. Additives such as silver show particular promise due to its safety and demonstrated antimicrobial effectiveness, and because the interaction with phenolics still leaves free phenolic residues available to interact with contaminants, thereby allowing for synergistic contaminant capture and inactivation.

The compositions can be coated on a range of porous and non-porous surfaces, and can be deposited instantaneously or over extended periods of time ranging from 1 second to more than 144 hours. The compositions in the coating can interact with contaminants on the molecular level and, importantly, can also filter out contaminants on the microscopic and macroscopic levels. The coatings can remain intact through certain washing protocols, for example with surfactants and machine washing and drying, and can be removed with harsher washing protocols using strong acids, strong bases, or strong oxidizing agents in sufficient concentration.

The novel compositions and coatings disclosed in this application can include phenolic molecules that can be hybridized with other materials, including various organic, polymeric, inorganic, metallic, synthetic and biological compounds and materials, for improved versatility, specific performance governing interactions, stability, and other properties, and/or incorporation with other technologies. The phenolic molecules do not need to be covalently polymerized or condensed to form the novel coatings disclosed herein.

Covalent polymerization can occur with phenolic molecules through various synthetic coupling routes and can occur spontaneously or be expedited by the introduction of oxidizing agents, oxidizing conditions, buffers, salts, or pH changes. The hydrolysis (fragmentation) and condensation (polymerization) of phenolic molecules naturally occurs with slow kinetics compared to the speed of metal-chelation by phenolics and phenolic-metal-phenolic bridging. Chelated metals can stabilize phenolic molecules and help prevent their polymerization and oxidation as is well demonstrated in the literature. Thus, present phenolic-containing coatings can have condensed or hydrolyzed molecules, and importantly, the coatings do not rely on the condensation or hydrolysis for film formation. Instead, the low-valent metals act as linkages between phenolic molecules, which results in formation of coatings on substrate surfaces. The interaction of the phenolic molecules with low-valent metals is illustrated by the spectroscopy results of FIGS. 3B through 3D, which show peak shifts due to interactions between silver and tannic acid phenolic molecules.

The present phenolic-containing coatings are deposited and stabilized primarily through the interaction of the phenolics to the substrate surface and through the interaction of the phenolics with bridging low-valent metals that hinder polymerization. As a result, the polymerization of the coatings disclosed herein is significantly less than 50%; that is, significantly less than half of the phenolic molecules will polymerize prior to coating formation.

The lower polymerization of the current coatings is in stark contrast to existing coatings that use dissolved oxygen and various salts and buffering conditions to achieve gradual polymerization, where the coatings gradually grow, generally over the course of hours to days. It is this polymerization as the phenolic molecules bond to form chains that results in coating formation for existing coatings. When covalently polymerized, often C—C and/or —C—O linkages are formed for nitrogen-free phenolic molecules. Nitrogen-containing phenolic molecules, such as dopamine, polymerize more readily through a variety of chemical reactions including C—C, C—N, C—O, and others. The present phenolic-containing coatings could therefore be thought of as forming in a discrete deposition step, while existing coatings form continuously and only stop when removed from the coating substrate or the precursor molecules are consumed or lose their reactivity.

Polymerized phenolics can range from a few hundred Daltons (Da), to kilo-Daltons (kDa), and likely even to mega-Daltons (MDa) in part because of the often irreversible nature of covalent bonds. Existing polymerized phenolic coatings are deposited using dissolved oxygen and can coat macroscopic substrates, which suggests that the phenolic polymer size in the extended network of the coatings can be macroscopic. Non-covalent interaction, such as pi-pi and hydrophobic interactions, generally exist in phenolic coatings, but these can generally be broken using various solvents.

Polymerization in phenolic-based coatings can have negative effects. For instance, polymerization consumes hydroxyl groups that reduces the ability for the phenolic molecules to bind to contaminants, binders, dopants, and additives, and hinders the stable chelation of metals. Additionally, covalently polymerized phenolic films tend to take much longer to form as they grow gradually during the covalent polymerization and oxidation process, and can form thicker coatings, which could hinder the industrial application and the breathability and functionality of the underlying substrate. Hence polymerized phenolic films tend to be used on solid, non-porous substrates.

Phenolic-containing coatings prepared with low-valent metals and low-valent metallic salts, such as silver(I) and silver nitrate, have the benefits of being deposited rapidly on substrates—in some instances, less than 1 second. Low-valent metals tend to have a charge of 1+ or 2+ in their ionic state, an oxidation state of I or II when coordinated, and can bind at 2 or 4 sites to chelators, respectively. Such phenolic-containing coatings with low-valent metals also tend to have a stable thickness after the initial deposition, and the coatings leave unreacted hydroxyl moieties capable of binding to contaminants Coating with low-valent metals also do not require specific pH, buffers, salts, or dissolved oxygen species. Moreover, phenolic-containing coatings assembled with low-valent metal ions, such as silver 1+, can remain colorless, as the metal ion can be incorporated into the coatings without a necessary reduction to colored silver nanoparticles, as seen in existing coatings. For prior art phenolic coatings, silver is incubated with pre-formed phenolic coatings for extended periods ranging from hours to days to allow for incorporation of the silver fully into the coatings, a significant issue for industrial translation. Phenolic-containing coatings prepared from low-valent metals such as silver have an added benefit where the phenolic molecules used for the coatings process largely remain intact on the molecular level, which is contrasted with covalently polymerized phenolic coatings where the molecular building blocks undergo extensive, often irreversible chemical transformation.

Other important properties include the ability of the present compositions to be used as a standard dye for a variety of aesthetic applications and as a binder for integration with other applications, such as fluid transports using controlled wettability such as hydrophilicity or hydrophobicity, chemical resistance to solvents, redox agents, and similar, conductivity using conductive phenolics and additives, precious metal capture from liquid environments and slurries, and moisture capture in arid environments. The compositions based on the phenolic molecules are safe, non-toxic, and odorless, and can be applied to surfaces with equipment of different sizes ranging from small handheld equipment, to benchtop equipment, to industrial large-scale equipment.

The compositions based on phenolic molecules have advantageous chemical properties that include the presence of multiple simultaneous molecular pathways for contaminant capture and inactivation. Additives can modulate the molecular pathways available for interacting with, and inactivating, contaminants.

Phenolic molecules are rich in hydroxyl moieties, and more specifically hydroxyl groups on or adjacent to aromatic groups, such as phenol (one hydroxyl on a benzene ring), catechol (two adjacent hydroxyl groups on a benzene ring), and gallol groups (three hydroxyl adjacent on a benzene ring), and other combinations and their derivatives. Free coordination sites on the phenolic coatings allow for capture and inactivation of organic contaminants including proteins, lipids, viruses, bacteria and fungi through denaturation, such as with the phenolics used in the tanning industry or to precipitate proteins in wine, and for the capture of inorganic contaminants such as metals, metal particles, dust, and soot particles through chelation and coordination. Hydroxyl moieties can hydrogen bond as acceptors or donors depending on the protonation state, allowing for the capture organic materials such as pollen, cell membranes, microbes, polymers, and dyes. Hydroxyl moieties can also chelate and thereby capture metals and metallic species individually or in combination with adjacent or distant hydroxyl moieties. Hydroxyl moieties can also exhibit hydrophobic forces depending on the protonation state and can capture various hydrophobic contaminants such as lipids, plastics, plastic debris, proteins, and microbes.

The aromatic regions of the phenolic compounds (i) can pi-stack with cations to allow the capture of contaminants such as metal ions and positively charged polymers and proteins, (ii) can interact with anions to allow the capture of some metal species and negatively charged polymers, such as nucleic acids and phospholipid membranes, and (iii) can interact with hydrophobic contaminants to capture proteins, lipids, plastics, organisms, dyes, etc., and similar contaminants. The charged groups of the phenolic compounds can electrostatically interact with contaminants to capture and neutralize contaminants that may have electrostatic charges such as pollen, and other contaminants with charge such as microbes.

The ability for phenolics to simultaneously exhibit these molecular pathways, even when in combination with certain additives or after contaminant capture, means that phenolic coatings can have broad spectrum application in various scenarios where diverse contaminants need to be captures, such as capturing pollen, viruses, and soot bacteria simultaneously. These interactions are non-exhaustive and are provided to illustrate some specific interactions that can occur between the coatings and contaminants.

The present compositions and methods address certain shortcomings and limitations in the art regarding the capture, exclusion, and inactivation of contaminants, particularly of microbes, volatile organic compounds, and metal-containing particulate matter and aerosols. These shortcomings in the art include the lack of an adhesive nature of prior compositions to various substrates and the limitation of prior compositions in displaying only single molecular interactions towards contaminants, and the limitation of thickness control and conformality of the coatings to ensure that the pores of the substrate such as masks, filters, and clothing, are not clogged after the coating. Moreover, the ability to capture and decontaminate through physical or chemical inactivation is not readily available in the current coating technologies. The following details serve to illustrate these issues.

Decontamination of air and liquid can be performed through various techniques such as ultraviolet ("UV") light irradiation, chemical treatment, or filtration. Filtration is a relatively safe and inexpensive technique applicable for various environments such as houses, industrial settings, water treatment and various media (liquid and gas) and contaminants. Generally, filters are made from layers of different organic materials, with various support and filtration layers depending on the desired filtration efficiency. A disadvantage is that filters typically rely on exclusion of particles by size, but many contaminants such as small microbes (e.g., viruses), molecular contaminants (e.g., gases and volatile organic compounds), and small particulate matter can penetrate filters and do not strongly react or immobilize on the filter fibers. Sometimes electrostatic fibers will be used in filters, but the charge is easily neutralized through changes in environmental conditions such as humidity, gas content, or exposure to sun. As a result of the neutralization, the electrostatic fibers may have reduced efficacy in the capture of uncharged contaminants, and the electrostatic fibers may lose activity after interacting with charged contaminants. Consequently, contaminants can penetrate filters, and either custom filter designs or combinations with UV or chemical treatment are required. An alternative approach to using UV or chemical treatments to boost the decontamination of filters is to use coatings on the filter fibers that have a high and broad-spectrum affinity for contaminants. Similar challenges exist for materials other than filters, such as walls or clothes, where passive decontamination would be desirable.

Ideally, compositions used to deposit coatings, such as the compositions disclosed here for decontamination, should be usable on all types of surfaces and easy to apply to surfaces. Applicant's compositions are also conformal to the surface and to any pores on the surface to prevent clogging. Applicant's compositions are non-toxic and allow for the capture, repellence, and/or inactivation of wide variety of contaminants, as opposed to effective just for particulate matter filtration as with most filter designs.

Moreover, the composition of the coating and deposition process should not harm the substrate to which the coating is applied. Important examples of porous materials where decontaminant coatings would be desirable, but for which coatings do not currently exist, include materials such as synthetic and natural fiber masks, clothing, walls, door handles, tiling and grout, and air and water filters, to name a few. Coatings should work against viruses, bacteria, fungi, spores, pollen, gases, volatile organic compounds, solvents, exhaust, particulate matter, smoke, heavy metals, and other similar contaminants. However, filtering these contaminants currently requires a variety of complex filtration and decontamination techniques most of which lack the general applicability of coatings. Applicant's compositions and coatings address the above-mentioned problems by providing robust, durable coatings that do not harm surfaces and that protect against a wide variety of microbes, contaminants, and other undesirable conditions, as explained in more detail below.

Molecules rich in catechol residues, where two hydroxyl residues are adjacent on a benzyl ring, or gallol residues with three adjacent hydroxyl residues on a benzyl ring, such as some phenolic compounds, can be used to create coatings capable of being deposited on nearly any substrate through a variety of techniques depending on the desired final properties and the phenolic used. A metal can be included to speed up the coating process. These metal and phenolic hybrid coatings can be used in microcapsule formulation in the biomedical sector. However, the generalizability to filtration and decontamination and substrates used for filtration and decontamination has thus far failed as coatings and are rarely explored for use in coatings purposes, and substrates used for filtration and decontamination are rarely modified before use. Moreover, these metal and phenolic coatings can sacrifice the adhesive nature of the phenolic molecule through the chelation with strongly chelating metal species, like the prototypical iron(III) used in most coatings. Post-functionalization of these metal and phenolic coatings with functional species is possible, however, the benefits of the phenolic molecule are not recovered in those instances. Finally, although ionic silver has been reduced to silver nanoparticles in phenolic coatings for antimicrobial applications, chelated silver (AgI) has thus far not been used in coatings to enable transparent and colorless antimicrobial coatings with higher efficacy.

Coatings derived from natural phenolics are also known. For example, tannic acid has been used to modify substrate surfaces. Some coatings require the use of multivalent (divalent and trivalent) metal ions ($Fe3+$, $V3+$, $Gd3+$, $Cu2+$ or $Cr3+$ ions) and relies on metal-oxygen coordination bonds formed between the tannic acid and multivalent metal ions for foil nation of the coating. However, these coordination-based coatings require a pH adjustment from acidic to basic to form and are restricted to certain metal types, do not last through washing steps, and are colored in most cases. Coatings that incorporate a polyphenolic, such as tannic acid, as one component of a multi-component coating have also been formed by a sequential deposition protocol named layer-by-layer technology. However, layer-by-layer coatings require large macromolecules and involve multi-step deposition processes lasting generally on the order of 10 minutes per deposition step where the macromolecules are separated into layers and less accessible to the surface and often have a turbid nature. Coatings comprised solely of polyphenols have also been prepared via polymerization. However, those prior approaches require specific pH and buffering conditions and long processing time for the polyphenols to polymerize in the presence of dissolved oxygen.

In the above instances, the polyphenolic coating can be incubated with silver ions or silver salts which is reduced to elemental silver in the coatings to form silver nanoparticles, which results in a dark appearance due to the color of silver nanoparticles. Furthermore, silver nanoparticles are inherently unstable, which prevents these coatings from being used long-term, through washing, and/or in complex environments. It is also desirable to avoid nanoparticles due to their potential negative health effects.

In contrast, the current phenolic-containing coatings can utilize ionic silver without resulting in discoloration as the silver is preserved in a chelated state. This possibility for monovalent metal ions to be chelated in polyphenol coatings was not thought possible without resulting in nanoparticles, which was as surprising find. As silver ions are 10-fold more potent antimicrobial agents than silver nanoparticles, and chelated silver is 10-fold more potent than silver ions, methods for creating chelated silver coatings, like the disclosure herein, are therefore of high priority.

Figure 3A:
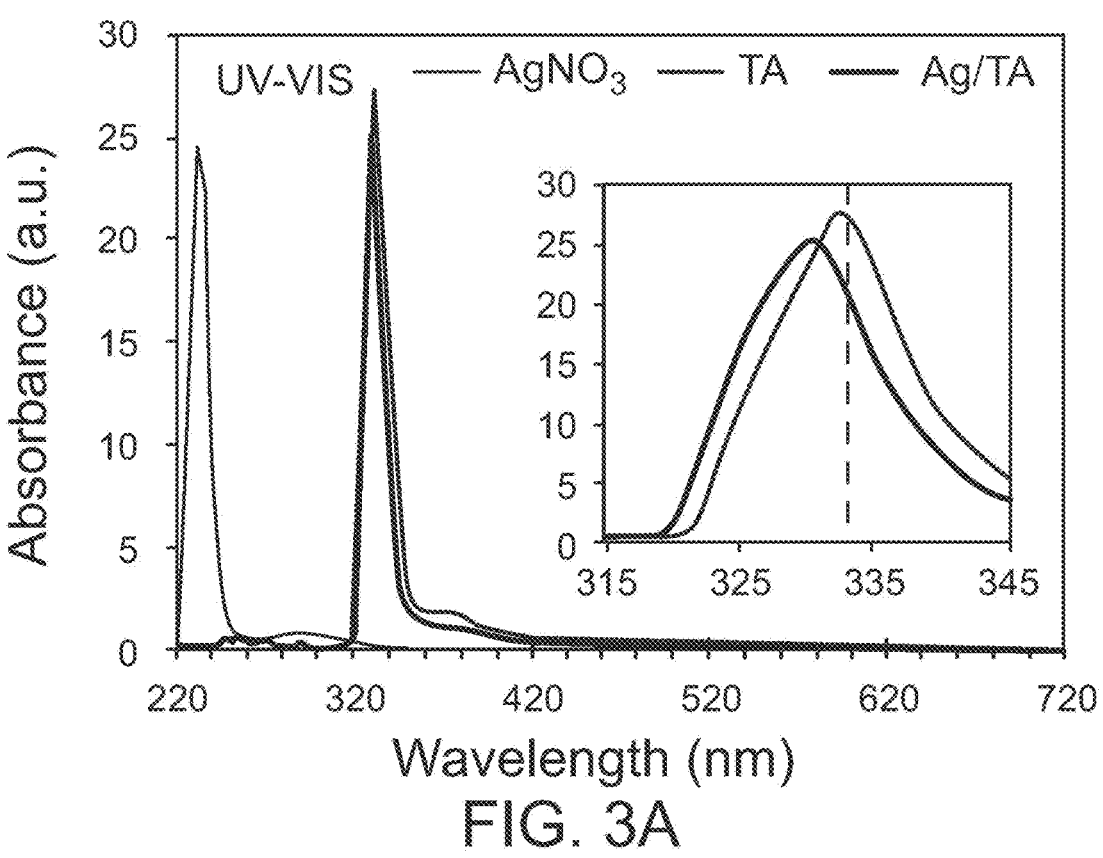
FIG. 3A illustrates experimental results for the ITV-Visible light absorbance properties of aqueous solutions of silver nitrate, tannic acid (phenolic molecule, TA), and silver/tannic acid (Ag/TA) complexes.
Figure 3B:
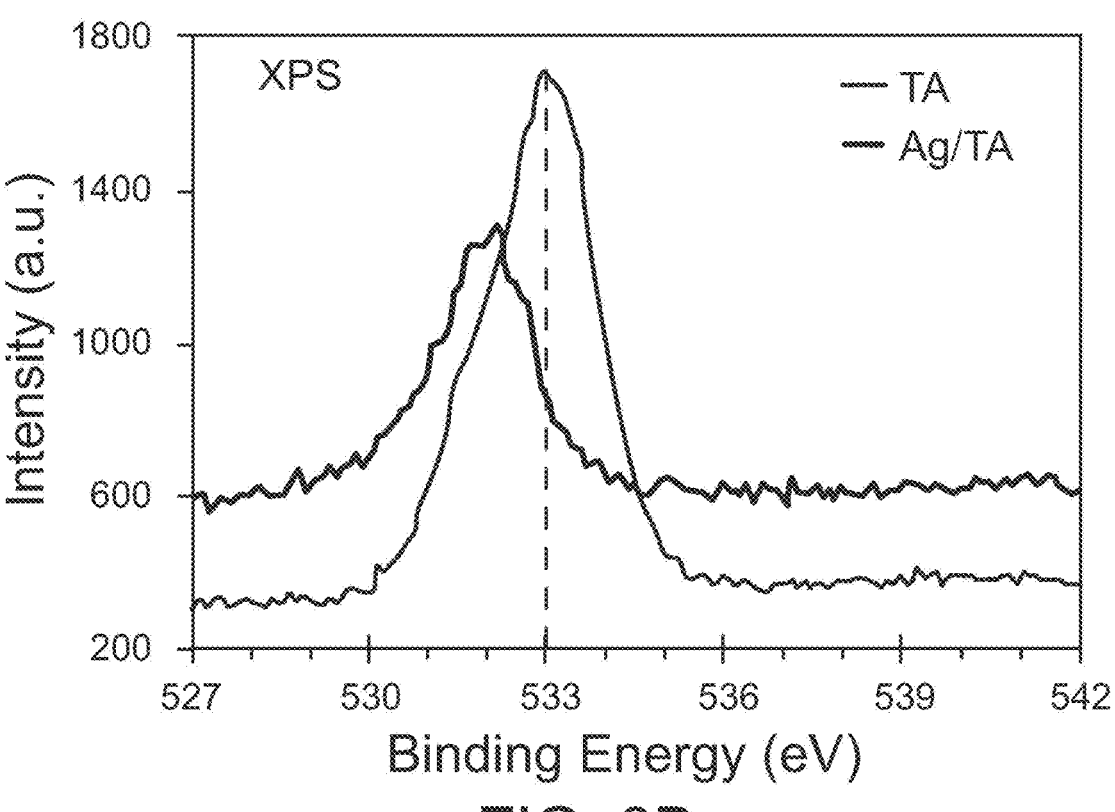
FIG. 3B illustrates experimental X-ray photoelectron spectroscopy results for the phenolic coatings prepared with silver on silicon in the $C_{1s}$ region. This peak shift arises due to interactions between silver and the phenolic molecule (tannic acid, TA).
Figure 3C:
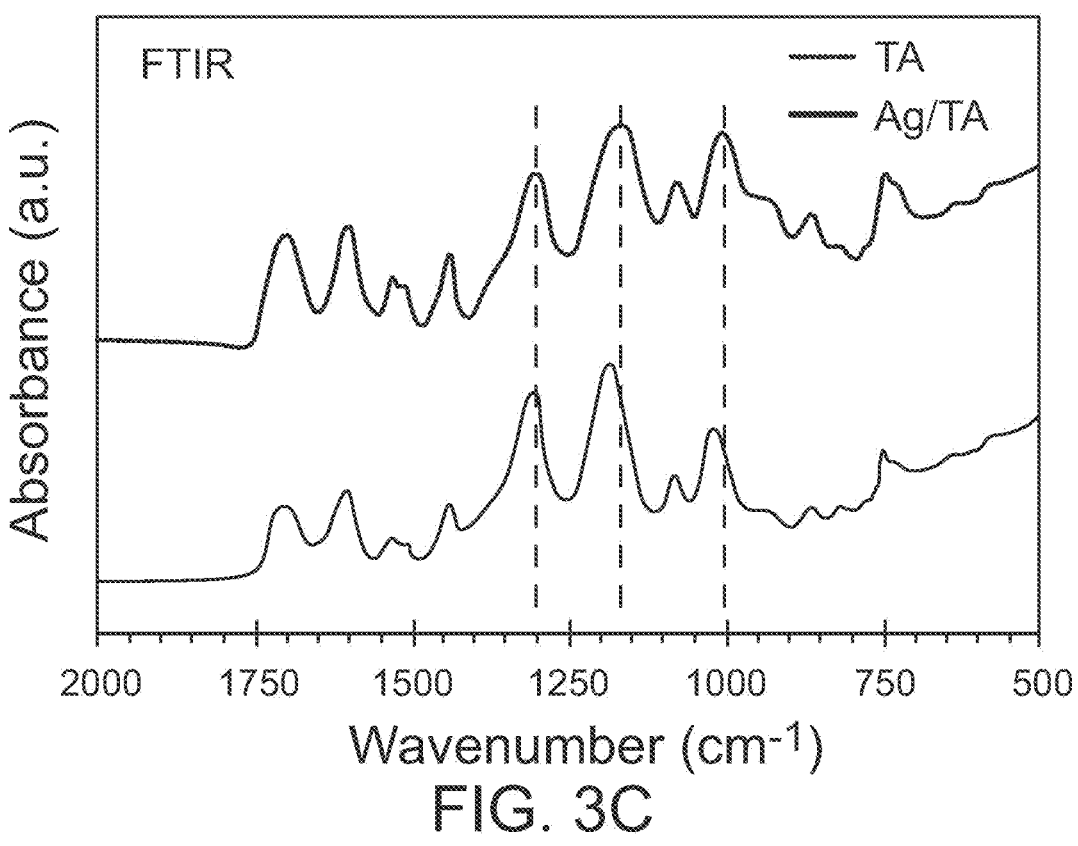
FIG. 3C illustrates experimental Fourier-transform infrared spectroscopy results for the phenolic coatings prepared with silver, highlighting peak shifts when silver is interacting with the phenolic molecule (tannic acid, TA).
Figure 3D:
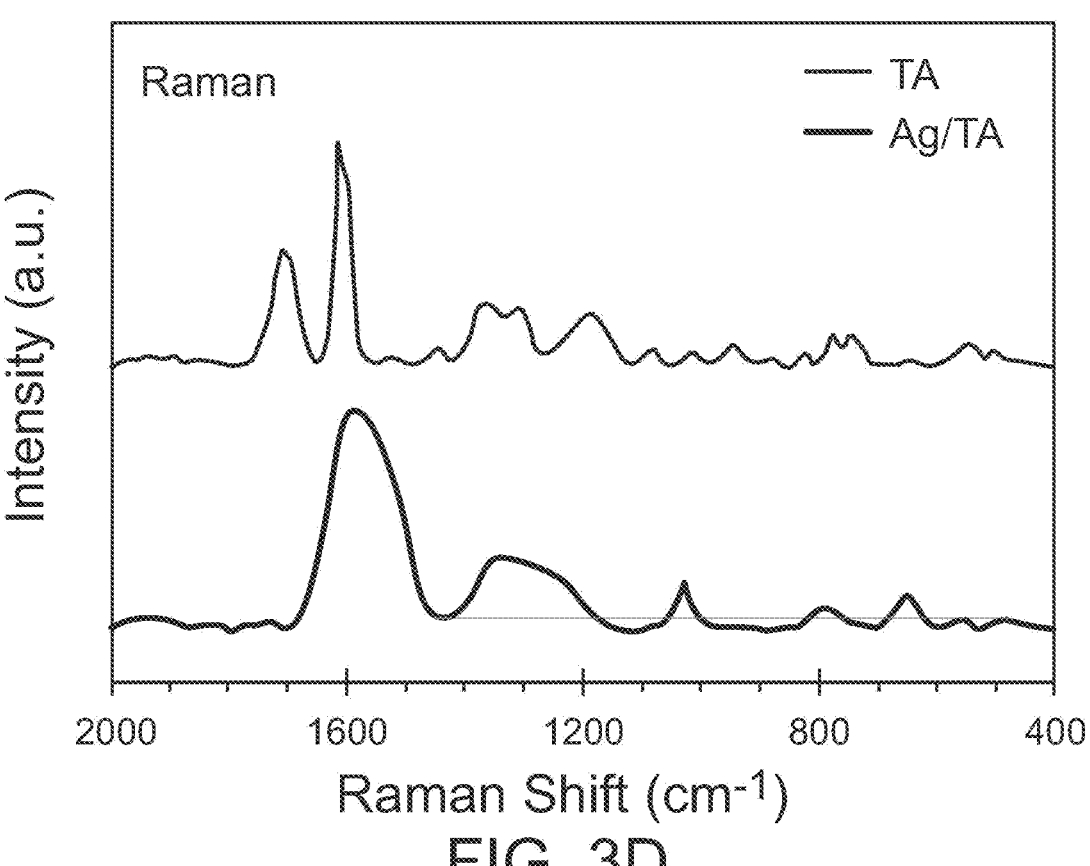
FIG. 3D illustrates experimental Raman spectroscopy results for the phenolic coatings prepared with silver, highlighting peak shifts when silver is interacting with the phenolic molecule (tannic acid, TA).
Figure 4A:
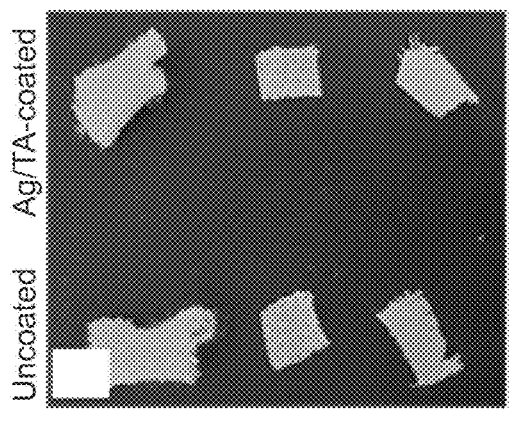
FIG. 4A illustrates experimental results for the colorless nature of the phenolic coatings prepared with silver on polyester, cotton, and silk as imaged with a camera on a white background.
Figure 4C:
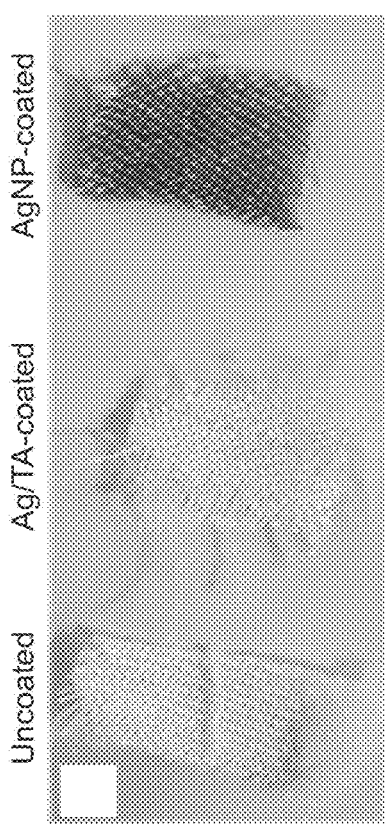
FIG. 4C illustrates experimental results for the colorless nature of the phenolic coatings prepared with silver compared to phenolic coatings with reduced silver nanoparticles as imaged with a camera on a white background.
Figure 4B:
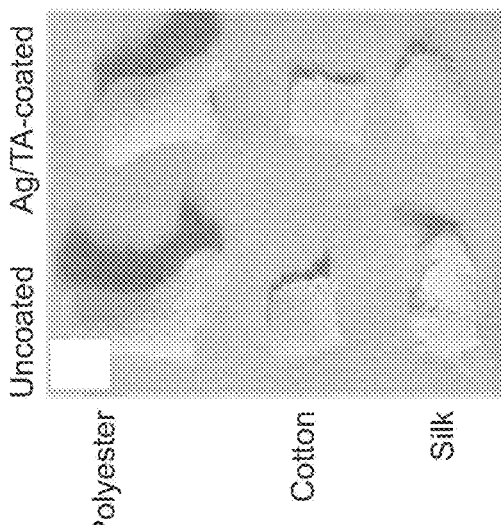
FIG. 4B illustrates experimental results for the colorless nature of the phenolic coatings prepared with silver on polyester, cotton, and silk as imaged with a camera on a black background.

Ionic and chelated silver is also transparent and colorless, which are aesthetically and practically beneficial properties, and when used with strong chelators such as phenolics, leach less than other silver-based antimicrobial technologies. FIGS. 4A and 4B illustrate experimental results for the colorless nature of the phenolic coatings prepared with silver on polyester, cotton, and silk. FIG. 4C shows the colorless nature of the current phenolic coatings prepared with silver compared to phenolic coatings with reduced silver nanoparticles. FIG. 3A illustrates experimental results for the UV-Visible light absorbance properties of aqueous solutions of silver nitrate, tannic acid (phenolic molecule, TA), and silver/tannic acid (Ag/TA) complexes. These results highlight the transparency in the visible light range of the phenolic complexes incorporating silver, and the absorbance in the UV range.

The present technology overcomes the foregoing shortcomings and limitations through the formation and use of phenolic-containing coatings for decontamination purposes. In particular, the present compositions and methods afford several benefits and advantages, including: (i) the ability to coat a wide variety (indeed, nearly all) substrates easily without requiring specialized equipment; use for decontaminating gas, liquid, or solid; (ii) presenting minimal or no toxicity; (iii) providing high levels of contaminant capture, inactivation, or exclusions due to complex chemistry of the coatings; (iv) reusability of the coatings due to the durable nature of the coatings with minimal leaching of the additives even during and after washing; (v) presenting minimal color; and (iv) versatility of including diverse additives.

The phenolic-containing coatings can be prepared from aqueous or organic solvents by dissolving one or more phenolic molecules at a concentration of 1 nano-mole (nM) to 10 moles (M). Coating preparation can optionally include dissolving a metal salt such as silver nitrate, silver chloride, copper chloride, zinc chloride, zirconyl chloride, and similar compounds. Coating preparation can also optionally include solvents mixed with (i) organic molecules such as antimicrobial agents, (ii) targeting ligands for biological capture, (iii) fluoropolymers for hydrophobicity, (iv) charged polymers such as quaternary ammoniums, (v) charged silanes and hemolytic polymers for capturing oppositely charged contaminants and disrupting the contaminants, and (vi) enzymes for catalysis, etc. The foregoing compounds are placed in a solvent to a final concentration of 1 nM to 10 M.

For example, antimicrobial metals such as silver, liquid gallium, copper, and their related alloys can be added to the coatings at a final concentration of 1 nM to 10 M during or after the coating process. Similarly, antimicrobial organic molecules can be incorporated during or after coating at a final concentration of 1 nM to 10 M, such as antibiotics, quaternary ammonium compounds, and related molecules, such as 2,4,4'-trichloro-2'-hydroxydiphenyl ether; diiodomethyl p-tolylsulfone; an azole such as propiconazole; polyhexamethylene biguanide hydrochloride; 3,4,4'-trichlorocarbanilide; or others. The phenolic solution can be deposited on a surface separately, or the phenolic solution can be mixed with the solution containing organic molecules or metals at a ratio between 1:100 to 100:1 phenolic to other compounds (either in organic or aqueous solvents). Further additives and dopants can be added at a ratio between 1:100 to 10000:1 phenolic to other compounds. The compound that includes organic molecules and metals can be added as a powder or can be separately dissolved in an aqueous or organic solvent and then added to the base phenolic compound before deposition or added to the base phenolic compound during deposition either simultaneously or in sequence. In other embodiments, the phenolic compound can be added to the other compound as a powder or by mixing the solutions in a similar fashion.

The deposition conditions can be carried out at room temperature without any additional energy input. Alternatively, one or more techniques using spraying, ultrasound, microwaves, vacuum, mechanical mixing, blotting, and flow reactions can also be used to facilitate deposition of the coating solution. The coating solution can be used to spray, drop-cast, blot, or other methods onto or into the substrate. Spraying can take place with aerosols or mists are a relative volume of 1 μL to 10 mL of coating solution per square centimeter. A substrate can be immersed into the coating to accomplish deposition, the coating can be mixed directly on the substrate, or the coating can be mixed before contact with the substrate. The deposition technique, and any subsequent washing steps can influence the properties of the coatings, such as thickness, porosity, color, and stability, and the performance of the coating, such as what specific contaminants it has a preference to capture and/or inactivate. Drying can be done by air, by tumbling, by heat, or by other individual and combinations of drying methods. For example, a spray-coated surface might only require 1 to 60 minutes for the solvent to evaporate under ambient conditions with low to moderate humidity, while a porous textile might require up to 24 hours to dry by air after immersive coating.

Additional functional cargo such as metal ions, metal nanoparticles, which are either intact or metal ions that will reduce or oxidize into nanoparticles, metal-organic particles, organic molecules, such as dyes, and/or biological molecules, such as enzymes can be incorporated during the synthesis stage at final concentrations ranging from 0.01 nM to 10 M, where the final concentration in the coating can be from 0.0001% by weight to 50% by weight. The functional cargo can be added before adding the respective final component if adding more than one component separately. The functional cargo can also be added to one or more of the solutions before or during coating or by addition subsequent to the coating process.

Various compounds can be incorporated as functional cargo components into the phenolic-containing coatings containing at least one phenolic. Functional cargo compounds or components can fill voids within the coatings and can be incorporated into pores within the coatings, or be bound to the coating or substrate, or otherwise contained in the coating. Porosity of the coatings can be tailored to adjust the amount of functional cargo incorporated therein. Examples of functional cargo compounds or components include organic molecules such as antimicrobial molecules, two dimensional materials such as graphene, inorganic molecules, various nanoparticles and microparticles, magnetic materials, catalytic materials, and biomolecules such as enzymes.

Other additional components such as various micro-particles can be incorporated in the composition. This allows the phenolic-containing coatings to be coupled with other decontamination materials, thereby retaining the positive aspects of the current phenolic-containing coating, while also receiving advantages from the incorporated cargo.

Addition of the phenolic-containing solution results in a thin film coating on the substrate that may take on the color of the phenolic compound depending on the thickness of the coating and the phentolic(s) used. Mixing of the phenolic-containing solution and other compound(s) can result in transparent, colored, or milky solutions where the color and opacity may be transferred to the substrate in the coating.

After addition to the substrate, the coated substrate can be subsequently washed using one or more washing steps with different solutions. The coating can optionally be washed with one or more drying steps via evaporation, blotting, wiping, blowing of air or other gases, heating, or cooling to remove unreacted compounds or to alter the physicochemical nature of the coating such as the pore size, charge, or other properties in between or after the washing step(s). The washing can be conducted with aqueous or organic solvents, where harsh solvents such as piranha, hydrochloric acid, sodium hydroxide, etc. are typically avoided, especially in higher concentrations. In certain instances, significant bound moisture may need to be removed before the full range of applications described herein can be achieved. After drying, the coating may be visible or invisible depending on the exact formulation.

Figure 3E:
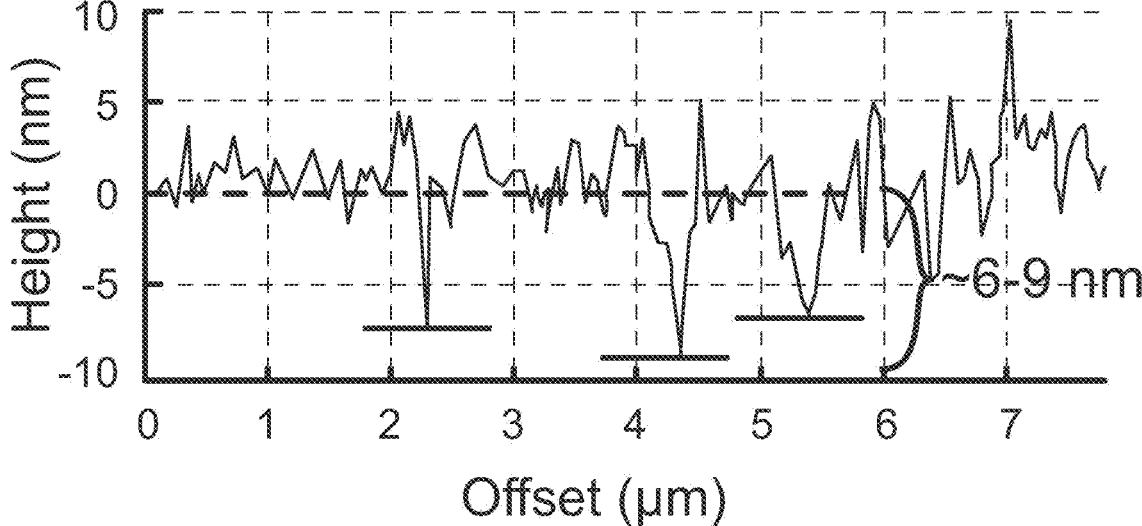
FIG. 3E illustrates experimental atomic force microscopy results for the material properties of phenolic coatings prepared with silver, demonstrating the thickness of the films on a silicon wafer.

The coating can form a film thinner than 2 nm, but generally will have a thickness on the order of 5 to 200 nm including where the film has an average thickness 200 nm or less. Above this thickness, significant bridging of any pores in the substrate is possible, which could negatively impact fluid flow through the original substrate and thereby hamper filtration, decontamination, breathability, or use in other desired applications, and the material wastage becomes more of an issue as more additives are needed for the same efficacy. FIG. 3E shows a thin phenolic coating of less than 10 nm prepared with silver formed on a silicon wafer substrate. The phenolic compound and the other compound can form coatings with discrete phenolic patches inhomogenously distributed on the surface, or the phenolic compounds can form network coatings fairly homogenously and uniformly deposited on the surface that include one or more types of phenolics and other atoms or molecules.

As a film, the phenolic-containing coating can be used with standard decontamination substrates such as masks and filters. The phenolic-containing coating can be used with substrates that can be contaminated with microbes during use such as clothing, underwear, sheets, fabric, toys, tile, grout, wood, plastic, metal, walls, wallpaper, sponges, or human skin. The phenolic-containing coatings can be used on any surface for imparting decontamination properties to the surface and substrate. The coatings can be deposited and used in controlled environments, industrial environments, household environments, or in field environments and other settings.

The phenolic-containing compounds can be removed from substrates using triggers dependent on the specific composition of the coatings. For example, when some chelating metals are using in conjunction with the phenolic compounds, the phenolic-containing coating can sometimes be removed in acidic environments or through the use of a stronger chelator such as ethylenediaminetetraacetic acid (EDTA) in excess. When a hydrophobic polymer is used in the phenolic-containing coating, the coating can sometimes be removed in organic solvent or in alkaline conditions. Surfactants will sometimes remove the phenolic-containing coatings depending on the coated substrate's surface chemistry. When the coating includes hydrophilic and/or charged compounds, the phenolic-containing coating can sometimes be removed in acidic environments or organic solvents. The phenolic-containing coatings can sometimes be regenerated where the captured contaminants are removed but the phenolic-containing coating is left behind. Depending on the type of substrate, regeneration can be accomplished using standard washing protocols, such as washing with soap and water.

Phenolic compounds are defined by the inclusion of at least one phenolic group, namely an aromatic hydrocarbon bonded with at least one hydroxyl group. Representative phenolic compounds can be natural or synthetic and include lignins, tannins, stilbenes flavonoids, phenolic acids, catechol and gallol-containing molecules, and similar classes of molecules. Specific illustrative examples include, but are not limited to, tannic acid, gallic acid, caffeic acid, resveratrol, persimmon tannin, grapeseed extract, gallnut extract, proanthocyanidins, pyrogallol, epigallocatechin gallate, pyrocatechol, catechin, or synthetic molecules modified with phenolic groups, among other compounds. The phenolic compound acts to anchor the coating to the substrate in most cases, and also provides decontamination properties to the coatings.

Additional compounds that can be added into phenolic-containing coatings include metal and organic compounds such as metal ions, metal salts, metal oxides, metal hydroxides, pure metals, polymers, small molecules, graphene, proteins, enzymes, dyes, and other compounds and molecules. The additional compounds may help in binding the phenolic-containing coating to a substrate (e.g., using metals and cationic polymers), may improve or alter the decontamination properties (e.g., metals, metal nanoparticles, polymers, enzymes, carbon-based materials), may make the coating more or less robust (depending on the charge of an added polymer, the chelation strength of an added metal, or the inclusion of silanes), may alter aesthetics of the coatings such as color or reflectivity (e.g., through the addition of a dye, specific metal, or nanoparticle), may alter the breathability of the coating (e.g., using graphene), may alter the wetting of the coating (e.g., using fluoropolymers or hydrophobic polymers and materials, or by using hydrophilic polymers), may change the antimicrobial specificity of the coating (e.g., using specific metals such as copper or silver, or using small molecule antimicrobial agents or peptide-based materials), may change the net or localized charge of the coating (e.g., using metals or charged polymers) or may change or alter other related properties of the coatings and how the coatings interact with contaminants, environments, and substrates.

A particularly advantageous aspect of the compositions for depositing phenolic-containing coatings is the strong binding to biological substrates, such as human skin. This makes the coatings especially useful for certain substrates that have so far been unsuitable and out of the operational range of decontamination and filtration coatings, such as cotton substrates (e.g, masks and clothes), wood (e.g, tables and chairs), cellulose (e.g., filters), silk (e.g., clothes and sheets), leather (e.g., clothes, car seats, wallets), among others.

Of particular note, the present phenolic-containing coatings can be used to capture materials from air, aerosols, droplets, and other fluid or vaporous materials. For example, particulate matter is often charged and can electrostatically interact with the phenolic-containing coatings. Phenolic coatings are highly wetting, and droplets or particles contained in water or moisture will spread rapidly. The wetting property allows the phenolic-containing coatings to directly contact contaminants such as microbes contained in liquid or vaporous materials and allows the phenolic coatings to more easily be deposited on surfaces.

The phenolic-containing coatings disclosed herein can also be used in arid environments where static charge becomes more common, and moisture does not need to be present for the coatings to be effective at neutralizing contaminants. The present phenolic-containing coatings can, therefore, provide substantial advantages in coating masks, PPE, and air filters.

Another important aspect of the novel phenolic-containing coatings is that the coatings also bind to biological contaminants in both wet and dry environments (e.g., water, saliva, mucus, air, oil, gas, dispersions). Moreover, the coatings also bind to synthetic and man-made contaminants in such environments. Most decontaminating coatings are limited to use in capturing contaminants in liquid, but the present phenolic-containing coatings are effective in dry and wet environments and with dry (e.g., particulate matter from combustion, heavy metal particles) and wet (e.g., sneezed fluids containing microbes, dissolved metals) contaminants. The wet and dry versatility makes the present coatings substantially more useful and more valuable as an all-purpose coating that can be used in various industries, applications, and environments for decontamination on a wide variety of surfaces.

Depending on the particular application, decontamination procedures can require specific procedures, filters, solutions, and coatings that may be used separately. Identifying the appropriate filters, solutions, and coatings to use for particular substrates or surfaces can be critical as most contaminants can evade multiple classes of materials, and certain filtering or decontaminating materials can be destroyed or irreversibly changed depending on the contaminants and processes employed. Therefore, the general coatings provided by the present technology can avoid these issues. What is more, certain chemical groups and functionalities can be incorporated into the phenolic-containing coatings to allow for further chemical modification and for integration with various sprays and substrates used in secondary methods.

Compositions including the phenolic-containing coating can be sterilized, and the coatings are non-toxic with regard to human and animal contact, thereby making the coatings useful for application to materials that may come into contact with skin. Once removed from a substrate, the coatings are environmentally benign, and phenolics are regular components of most water systems. Any other additives will retain their original properties and compositions or be surrounded in phenolics upon coating removal, thereby partially neutralizing them. The coatings can adhere through washing steps in many formulations, which allows for the coating of masks and clothing safely, as the materials can be washed in conventional laundry settings and apparatuses without impacting laundering equipment or effluent.

Various compositions including the phenolic-containing coatings can be formed and used. These include various colorless and colored solutions, coatings with specific catalytic qualities, and coatings that include additional functional properties. As one example, colorless coatings can be formed by first dissolving tannic acid (TA) at a concentration of 0.24 M in 1 L water and separately a mixture of silver nitrate dissolved at 0.24 M in 1 L of water. These solutions can be combined together in a large flask and thoroughly mixed by shaking or sonication, for example. The resulting solution can then be used and deposited on substrates by spraying, dipping, or other suitable techniques. Various intermediary phenolics and chelators or organic linkers other than tannic acid, such as gallic acid, lignin, catechol polymers, etc. can be used in combination with, or instead of, TA for coatings and decontamination purposes, to change the coating stability, color, or to alter the decontamination ability or speed. The aforementioned metal salt solutions for the colored coatings can be mixed with nanoparticles, such as liquid gallium nanoparticles, silver nanoparticles, copper and alloyed copper nanoparticles, at weight concentration between 0.001% and 25%. As another example, colored coatings, such as pink can be formed by adding a dye into the coating solutions at weight concentrations between 0.001% and 5%. As still another example, chemical functionality can be added to the coatings, where a phenol-modified polymer, such as a low-fouling polymer like PEG-catechol or poly(oxazoline)-catechol, can be used in conjunction or in place of TA in the above formulations to reduce the biofouling properties of the coatings, for example for catheters. Simila As another example, reactive polymers can be chemically linked to pre-make phenolic coatings. As another example, antimicrobial metals or organic molecules can be post-infiltrated into or onto the coatings. Combinations of these above examples are also possible and expected.

WORKING EXAMPLES

Examples 1-6 relate to compositions of the phenolic-containing coatings that are applied using a single solution. Examples 7-11 relate to using 2 or more solutions. Examples 12-15 relate to a depositing the coating on large substrates. Examples 16-18 relate to different washing and drying scenarios for phenolic-containing coatings where the coatings are kept functional after washing. Example 19 relates to using a washing protocol to fully remove the phenolic-containing coatings from a substrate.

Example 1

Use of a Mono-component Phenolic-containing Coating on Masks for Virus Capture A single solution of tannic acid at 10 mg/mL in ethanol is sprayed onto a mask 10 times using a standard mist sprayer with mist volumes of 0.05 mL per spray. The coating is left to dry for 5 min, and then the mask is used normally. Aerosolized virus and virus contained in droplets can be stopped by the mask, and the tannic acid binds to the virus, preventing its transport. The mask can be re-sprayed with the phenolic-containing coating for re-use after optional washing.

Example 2

Use of a Single Solution of Multi-components Phenolic-containing Coating on Grout for Protection From Mildew Grout and tiling covering 1 square meter are sprayed with a single solution of 1 mg/mL tannic acid and 0.25 mg/mL silver nitrate in water at spray volumes of 1 mL per spray and 1 spray per 5 square centimeters and left on the grout and tile for 5 min. The solution is then rinsed off with excess water and left to dry for 12 h. The grout and tiles are then protected against mildew and will be infiltrated by microbes at a slower rate than uncoated grout.

Example 3

Use of a Single Solution of Multi-components Phenolic-containing Coating on Wood for Protection From Mildew and Termites Wood of 1 square meter is sprayed with a single solution of 1 mg/mL tannic acid and 1 mg/mL silver nitrate in water at a continuous spray for 10 min, equating to 1 L of solution sprayed. After 1 minute, the wood is rinsed with water and left to dry in an oven for 6 hours at 50° C. The wood is then protected against mildew and termites.

Example 4

Use of a Single Solution Multi-components Phenolic-containing Coating on a Door Handle for Antimicrobial Activity and Capture A single solution of tannic acid of 40 mg/mL and CuCl2 of 10 mg/mL in ethanol is sprayed 20 times onto a door handle at 10 μL per spray and left to dry for 30 min. The tannic acid can capture microbes on contact, while the copper can kill the microbes present on the coating. The coating can be mechanically removed by washing with soap and water and a strong abrasive sponge.

Example 5

Use of a Single Solution Multi-components Phenolic-containing Coating on a Shirt for Antimicrobial Activity A shirt is immersed into 10 L of a single solution of tannic acid of 0.4 mg/mL and AgNO3 of 0.1 mg/mL in water, removed from the solution after 5 min, rinsed with excess water 3 times, and dried in a mechanical heated tumble dryer. The tannic acid can capture microbes on contact, while the silver can kill the microbes present on the coating. The coating can last through machine washing with soap and water and machine drying until the individual fibers of the shirt start to fray.

Example 6

Use of a Single Solution Multi-components Phenolic-containing Coating on Shoes for Antimicrobial Activity and Odor Prevention A single solution of tannic acid of 1 mg/mL and AgNO3 of 1 mg/mL in water is sprayed onto shoes at 50 μL per spray and 4 sprays total and left to dry for 10 hours at low to moderate humidity. The tannic acid can capture microbes on contact, while the silver can kill the microbes present on the coating, including odor-causing microbes.

Example 7

Use of Two Solutions to Form Multi-component Phenolic-containing Coating on a Mask for Antimicrobial Activity and Pollution Capture A solution of grape seed extract of 0.4 mg/mL in water is sprayed onto a mask 5 times at a spray volume of 50 μL followed by an equal number and sprays of a solution of AgNO3 of 0.1 mg/mL in water. The sprayed mask is left to dry for 1 hour. The grape seed extract can capture microbes and pollution on contact, while the silver can kill the microbes present on the coating and inactivate certain volatile organic compounds.

Example 8

Use of Two Solutions to Form Multi-Component Phenolic-Containing Coating on a Bathmat for Antimicrobial Activity and Odor Prevention A solution of gallnut extract of 0.4 mg/mL in water is sprayed onto a bathmat followed by spraying with a separate solution of AgNO3 of 0.1 mg/mL in water, with 10 mL of both solutions sprayed. This coated bathmat is left for 5 min and then tumble dried at low heat and the gallnut extract can capture microbes on contact, while the silver can kill the microbes present on the coating, including odor-causing microbes. The bathmat can be washed normally by hand or in a washing machine with detergent with the coating remaining intact.

Example 9

Use of Three Solutions to Form Multi-component Phenolic-containing Coating on a Filter for Antimicrobial Activity and Pollution Capture A solution of tannic acid of 0.4 mg/mL in ethanol is sprayed onto a filter simultaneously with a solution of didecyldimethylammonium chloride of 0.01 mg/mL in chloroform with a total volume of 100 mL sprayed per square meter of filter. Then a solution of CuCl2 at 0.05 mg/mL in water is sprayed onto the filter, and the filter is left to dry in an oven for 48 hours at 40° C. The metal and organic antimicrobials can work synergistically together.

Example 10

Use of Three Solutions to Form Multi-component Phenolic-containing Coating on Fabric for Antimicrobial Activity and Odor Prevention A solution of tannic acid of 4 mg/mL in ethanol is sprayed onto a fabric simultaneously with a solution of reactive silane quaternary ammoniums of 1 mg/mL in water for a total spray volume of 10 mL per square meter. Then 1 mL of a solution of AgNO3 at 0.5 mg/mL in water is sprayed onto the fabric and left to dry for 10 h. The metal and organic quaternary ammonium can work synergistically together as antimicrobials.

Example 11

Use of Two Solutions to Form Multi-Component Phenolic-Containing Coating with Silver Nitrate on a Mask One solution includes tannic acid in a first chamber, and a second solution includes silver nitrate in a second chamber. Both the first and second solution are dissolved in either 100% water or a 5% ethanol/water solution. The first and second solution are applied together as a spray of 50 μL per spray to successfully form a silver-tannic acid network antimicrobial and anti-pollution coating with optional washing. The mask is then left to air-dry for 15 minutes before use and can be machine washed and dried normally.

Application can utilize a two-chamber spray bottle for convenient consumer use and application of the coating. An example process for depositing the coating using sprays followed by a wash are illustrated in FIG. 1A, which illustrates the use of separate solutions of tannic acid and silver nitrate, either sequentially or simultaneously, where washing with water is optional after coating.

Example 12

Fabric is Rolled Through Solutions to Form the Phenolic-Containing Coatings

Using standard roll-to-roll practices, fabric is rolled through an excess solution of 10 mg/mL tannic acid in water, then a washing solution, then an excess solution of 1 mg/mL of PEG-catechol in water, then a washing solution, then an excess solution of 1 mg/mL AgNO3 in water, and then a washing solution, where the washing solutions are buffered water. The fabric is then machine dried under heat, cut, and used normally.

Example 13

Solutions are Exhausted Onto Fabric to Form the Phenolic-containing Coatings Using standard exhausting practices, fabric is exhausted by a mixed solution of 1 mg/mL gallnut extract and 0.01 mg/mL dye in water for a total volume of exhaustion of 50 mL per square meter, then a solution of 1 mg/mL AgNO3 in water is exhausted onto the fabric at 100 mL per square meter. The fabric is then post-processed normally.

Example 14

Fabric is Blotted With Solutions to Form the Phenolic-containing Coatings

Using standard blotting practices, fabric is blotted by an excess solution of 0.4 mg/mL tannic acid in water, then by an excess solution of 0.1 mg/mL polyhexamethylene biguanide hydrochloride. The fabric is left for 2 min then post-processed normally and can be machine washed and dried without losing the antimicrobial functionality of the phenolic-containing coating arising from the phenolic and the added organic antimicrobial agent.

Example 15

Fabric is Blotted With Solutions to Form the Colored Phenolic-containing Coatings Using standard blotting practices, fabric is blotted by an excess solution of 0.4 mg/mL tannic acid and 0.001 mg/mL of an excess solution of azoic dye in water, then by an excess solution of 0.1 mg/mL of AgNO3 in water. The fabric is then post-processed normally.

Figure 1B:
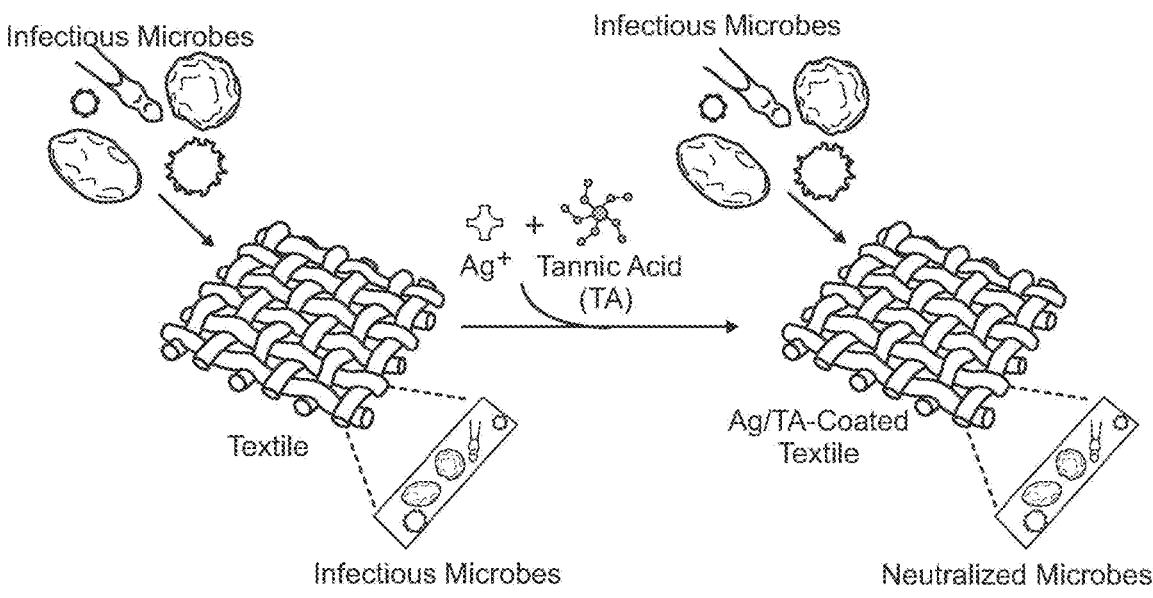
FIG. 1B illustrates a method for applying a phenolic coating of tannic acid and silver nitrate to a fabric.

FIG. 1B illustrates formation of a phenolic coating of tannic acid and silver nitrate on a fabric and highlights the neutralization of microbes on the coated textile. The phenolic coating can be formed with spraying or other techniques, such as blotting or immersion in a mixed silver nitrate and tannic acid solution, for example.

Example 16

Laundering a Shirt Coated With Phenolic-containing Coatings in a Washing Machine and Dryer A shirt coated with phenolic-containing coatings prepared from silver nitrate and tannic acid is added into a washing machine and standard laundry detergent is added at the amount recommended by the supplier. The shirt is washed on a standard rinse cycle with warm water, and after washing is added into a dryer. The shirt is then dried under a heat and tumbling cycle and is ready for wear with the phenolic-containing coatings still functional. Experimental data for this process is given in FIG. 8 for anti-odor applications.

Figure 8A:
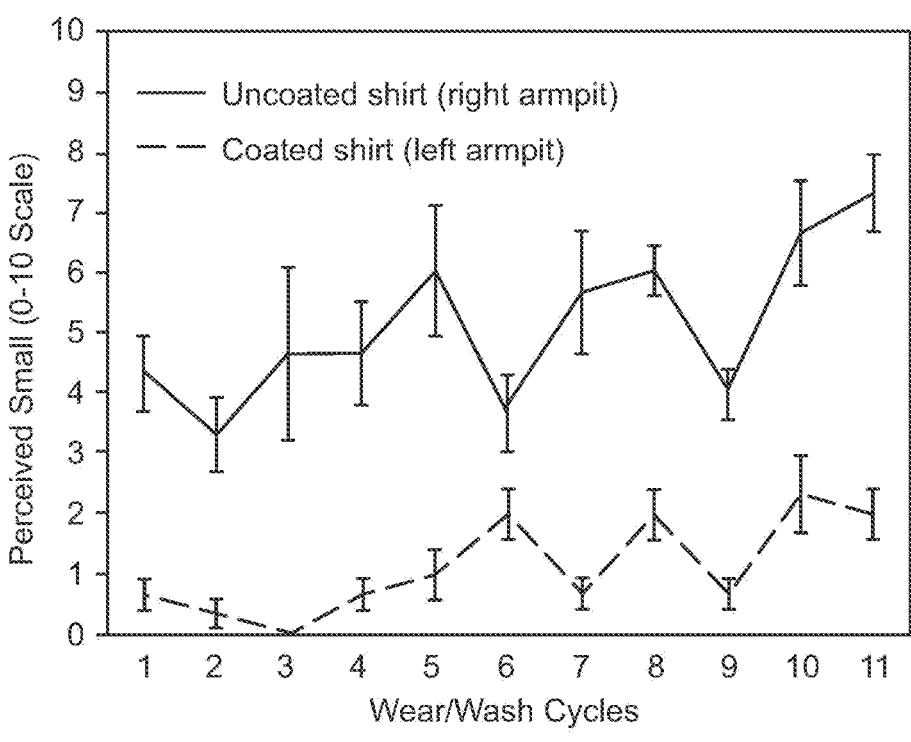
FIG. 8A illustrates experimental results for the anti-odor properties of the phenolic coatings prepared with silver, including specifically the perceived smell after a full day of wear comparing the left armpit of a shirt coated with phenolic coatings prepared with silver versus the right armpit that had no coating, as a function of the number of wash cycles.

FIG. 8A illustrates experimental results for the anti-odor properties of the phenolic coatings prepared with silver, including specifically the perceived smell after a full day of wear comparing the left armpit of a shirt coated with phenolic coatings prepared with silver versus the right armpit that had no coating, as a function of the number of wash cycles.

Figure 8B:
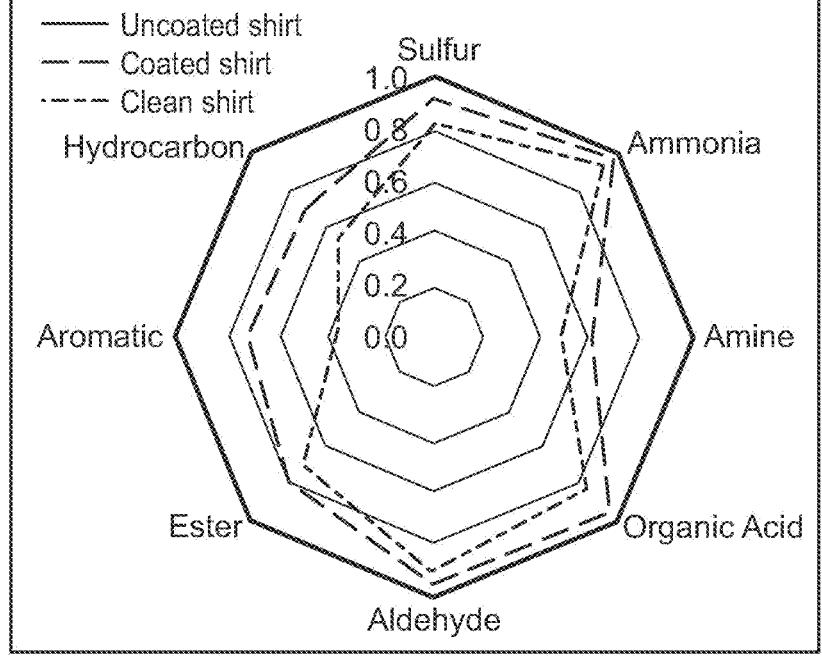
FIG. 8B illustrates experimental results for the anti-odor properties of the phenolic coatings prepared with silver, including a normalized odor comparison compared to various chemical compounds.

FIG. 8B illustrates experimental results for the anti-odor properties of the phenolic coatings prepared with silver, including a normalized odor comparison compared to various chemical compounds. The normalized odor composition of fabric from the same shirt before wear (clean shirt) and after wearing (comparing phenolic coatings prepared with silver (coated shirt) of the left armpit against the uncoated right armpit (uncoated shirt)) was measured by olfactometry using a Shimadzu Fragrance and Flavor Analyzer FF-2020. Note that the shirt was composed of synthetic fibers, was purchased new and washed only once before experimentation.

Figure 8C:
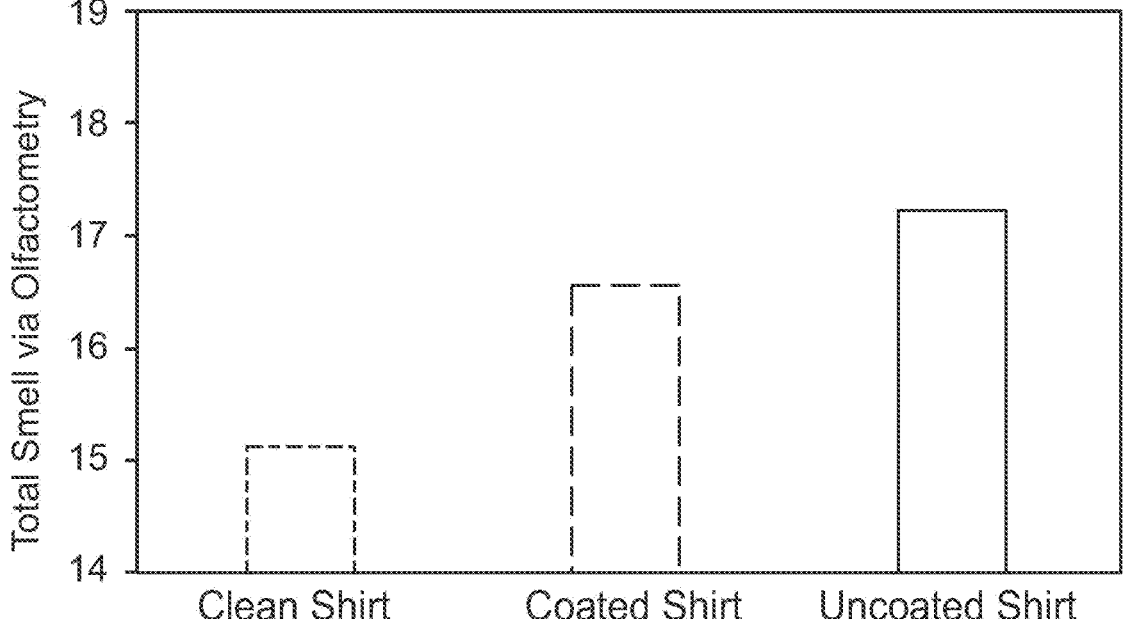
FIG. 8C illustrates experimental results for the anti-odor properties of the phenolic coatings prepared with silver.

FIG. 8C illustrates experimental results for the anti-odor properties of the phenolic coatings prepared with silver. The total smell was analyzed for fabric from the same shirt before wear (clean shirt) and after wearing (comparing phenolic coatings prepared with silver (coated shirt) of the left armpit against the uncoated right armpit (uncoated shirt)) by olfactometry using a Shimadzu Fragrance and Flavor Analyzer FF-2020. Note that the shirt was composed of synthetic fibers, was purchased new and washed only once before experimentation.

Example 17

Washing By Hand and Air-drying a Silk Mask Coated With a Phenolic-containing Coating A mask coated with phenolic-containing coatings prepared from silver nitrate and tannic acid is rinsed under excess running water and washed by hand with soap. The soap is then rinsed out of the mask with excess water and the mask is hung to air-dry for 12 hours. After drying, the mask is ready for wear with the phenolic-containing coatings still functional. Experimental data for this process is given in FIG. 5 for antiviral applications.

Example 18

Washing and Sterilizing Bandages Coated With Phenolic-containing Coatings

After wearing for wound healing applications, a bandage coated with phenolic-containing coatings prepared from silver nitrate and tannic acid is sterilized in an autoclave. It is then machine washed with laundry detergent and dried in a dryer. After drying, the bandage is ready for re-use with the phenolic-containing coatings still functional.

Example 19

Washing a Shirt Coated With Phenolic-containing Coatings With Harsh Solvents to Remove the Coatings A shirt coated with phenolic-containing coatings prepared from silver nitrate and tannic acid is soaked in either 0.1M HCl, 0.1M NaOH, or 1M H2O2, namely in strong acid, in strong base, or in a strong oxidizing agent. After soaking for 60 min, the shirt is removed, rinsed with excess water, and the phenolic-containing coatings are largely removed returning the shirt to near its original state.

Applicant's results for Examples 12, 4, 5, 6, 8, 11 were unexpected as prior to Applicant's research, it was not thought to be possible to make direct coatings of tannic acid and noble materials, especially silver, without discoloration and/or formation of nanoparticles, and additionally was surprising that such coatings did not compromise and actually increased the binding affinity of tannic acid in the coating to viruses and that the antimicrobial efficacy of silver remained after multiple washes.

Significantly, the viral binding affinity and inactivation ability of tannic acid and silver is shown in FIG. 2 to be superior to the performance of tannic acid with other metals.

FIGS. 3 and 4 show the material properties of tannic acid and silver coatings and their transparency and lack of color, which is surprising, especially compared with phenolic coatings containing silver nanoparticles.

Figures 5, 6:
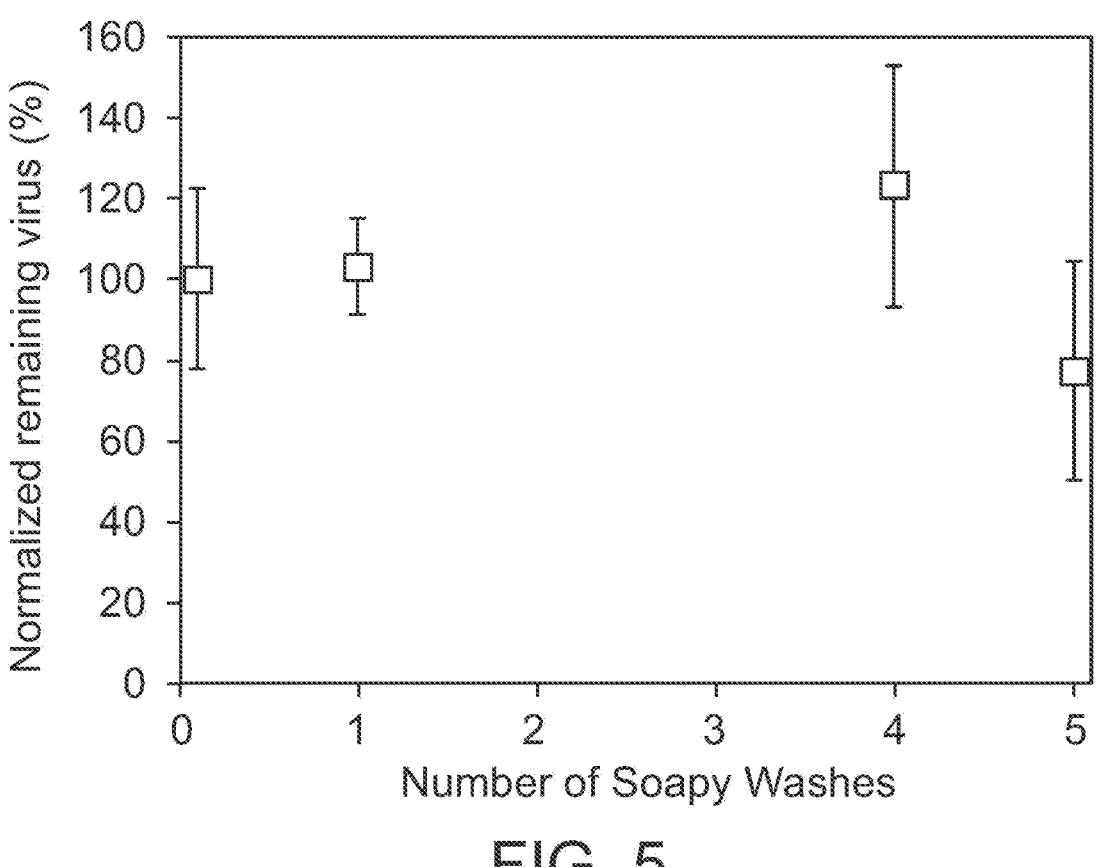
FIG. 5 illustrates experimental results for the viral reduction (Phi6) of the phenolic coatings prepared with silver on silk after different washing steps.
FIG. 6 illustrates experimental results on how different phenolics including tannic acid and persimmon tannin can be deposited with silver to form antiviral coatings (against Phi6) on silk.

FIG. 5 shows that tannic acid and silver coatings can maintain their antiviral activity even after multiple washes, which is surprising.

Figures 7A, 7B:
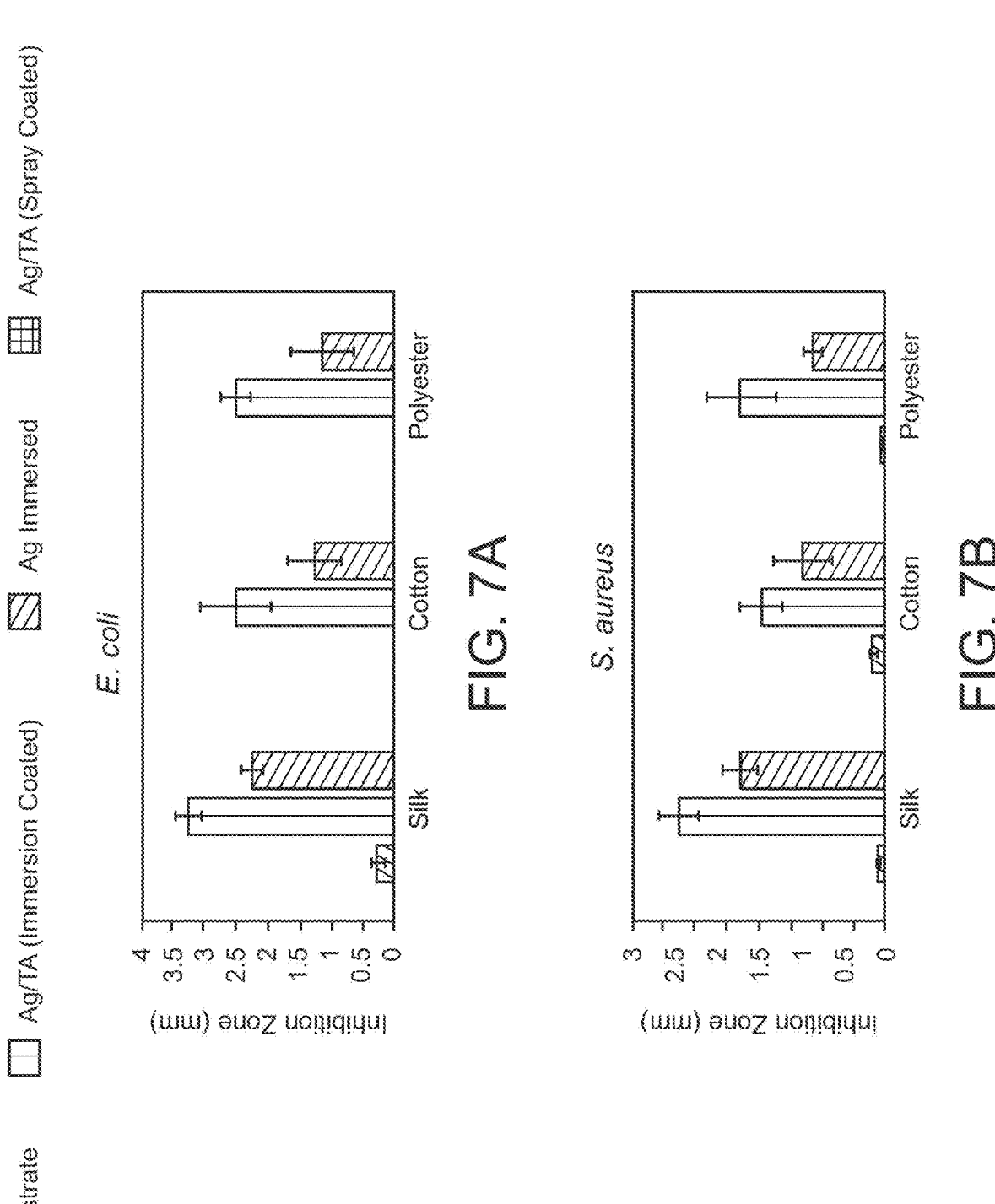
FIG. 7A illustrates experimental results for the antimicrobial nature of the phenolic coatings prepared with silver against Escherichia coli on materials that include silk, cotton, and polyester compared against bare substrates and substrates immersed only in silver nitrate solution.
FIG. 7B illustrates experimental results for the antimicrobial nature of the phenolic coatings prepared with silver against Staphylococcus aureus on materials that include silk, cotton, and polyester compared against bare substrates and substrates immersed only in silver nitrate solution.
Figures 7C, 7D:
FIG. 7C illustrates experimental results for the antimicrobial nature of the phenolic coatings prepared with silver against Saccharomyces cerevisiae on materials that include silk, cotton, and polyester compared against bare substrates and substrates immersed only in silver nitrate solution.
FIG. 7D illustrates experimental results for the antimicrobial nature of the phenolic coatings prepared with silver using immersion against Escherichia coli on materials that include silk, cotton, and polyester compared against bare substrates and phenolic coatings prepared with silver using spraying.
Figure 9:
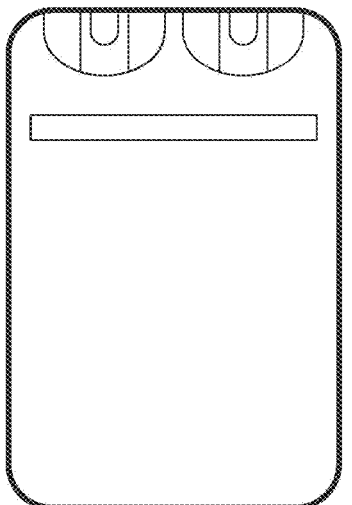
FIG. 9 illustrates a dual-chamber spray bottle used to deposit phenolic and silver solutions either simultaneously or sequentially onto different surfaces.
Figure 9:

FIG. 6 shows that other phenolic molecules such as persimmon tannin can be used instead of tannic acid for creating antimicrobial decontamination coatings with silver. FIG. 7 shows that tannic acid and silver coatings are effective against bacteria and fungi. FIG. 8 shows the anti-odor properties of tannic acid and silver coatings on clothes. FIG. 9 shows a small and portable two-chambered spray bottle capable of being used to apply tannic acid and silver coatings to different substrates and surfaces.

Although the foregoing description provides embodiments of the invention by way of example, it is envisioned that other embodiments may perform similar functions and/or achieve similar results. Any and all such equivalent embodiments and examples are within the scope of the present invention.

What is claimed is:

1. A method of forming a coating on a substrate comprising the steps of:
   (a) providing a solution consisting of a phenolic compound and a low-valent metallic salt both placed in a solvent, wherein
      (i) the phenolic compound comprises phenolic molecules and the low-valent metallic salt comprises metal ions that chelate to link the phenolic molecules,
      (ii) the phenolic compound is present in the solution at a concentration between 0.001 mg/mL and 50 mg/mL, and
      (iii) less than 50% of the phenolic molecules are covalently polymerized; and
   (b) contacting at least part of a substrate with the solution, wherein the phenolic molecules create a coating disposed on the substrate.

2. The method of forming a coating of claim 1, wherein the phenolic molecules comprise at least two adjacent hydroxyl groups.

3. The method of forming a coating of claim 1, wherein the phenolic compound is selected from one or more of tannic acid, gallic acid, caffeic acid, resveratrol, persimmon tannin, grapeseed extract, gallnut extract, proanthocyanidins, pyrogallol, epigallocatechin gallate, pyrocatechol, or catechin.

4. The method of forming a coating of claim 1, wherein:

(a) the phenolic compound comprises tannic acid at a concentration between 0.004 mg/mL and 1.5 mg/mL; and
   (b) the solvent comprises water.

5. The method of forming a coating of claim 1, wherein:
   (a) the phenolic compound comprises tannic acid at a concentration between 1 mg/ml and 12 mg/mL; and
   (b) the solvent comprises an ethanol solution.

6. The method of forming a coating of claim 1, wherein the low-valent metallic salt is selected from one or more of silver nitrate, silver chloride, copper chloride, zinc chloride, or zirconyl chloride.

7. The method of forming a coating of claim 6, wherein:
   (a) the phenolic molecules bind to the substrate;
   (b) the substrate is washed with a soap; and
   (c) the coating remains disposed on the substrate following the wash.

8. The method of forming a coating of claim 1, wherein the low-valent metallic salt comprises silver.

9. The method of forming a coating of claim 8, wherein the low-valent metallic salt is selected from one or more of silver sulfide, silver bromide, silver iodide, 2-benzothiazolethiol silver salt, saccharin silver salt, 2-cyano-hydroxyimino-acetamide silver salt, phosphoenolpyruvic acid silver barium salt, 4-hydroxy-1 (2H)-phthalazinone silver salt, silver lactate, silver acetate, silver citrate, Silver 2,4-pentanedionate, Silver benzoate hydrate, silver arsenate, mercury (II) silver iodide, silver carbonate, silver chromate, silver cyanate, silver cyanide, silver cyclohexanebutyrate, silver diethyldithiocarbamate, silver heptafluorobutyrate, silver hexafluorobutyrate, potassium silver cyanide, silver behenate, silver fluoride, silver hydrogenfluoride, silver hexafluoroarsenate, Silver hexafluorophosphate, silver hexafluoroantimonate, silver oxide, silver iodate, silver tetraborate, silver methanesulfonate, silver molybdenum oxide, silver perchlorate, silver phosphate, silver perrhenate, Silver p-toluenesulfonate, silver sulfide, silver tetrafluoroborate, silver thiocyanate, silver trifluoromethanesulfonate, silver tungsten oxide, silver trifluoroacetate, or Silver sulfadiazine.

10. The method of forming a coating of claim 1, wherein the low-valent metallic salt comprises silver nitrate.

11. The method of forming a coating of claim 10, wherein silver nitrate is present in the solution at a concentration between 0.04 mg/mL and 1.5 mg/mL.

12. The method of forming a coating of claim 1, wherein the step of contacting the substrate with the solution comprises spraying the solution on the substrate.

13. The method of forming a coating of claim 12, wherein:
   (a) the step of contacting the substrate with the solution comprises spraying the solution on the substrate with a spray volume between 1 μL to 10 mL per square centimeter of the substrate; and wherein
   (b) the method of forming a coating further comprises the step of allowing the substrate to dry for at least 60 seconds.

14. The method of forming a coating of claim 12, wherein: (a) a coating is formed on the substrate after 60 seconds; and (b) the coating is less than 200 nanometers in thickness.

15. The method of forming a coating of claim 1, wherein the substrate comprises a one of: (i) fabric, (ii) a facial mask, (iii) a filter, (iv) a wood surface, (v) a metal surface, (vi) a painted surface, (vii) a glass surface, (viii) a plastic surface, (ix) a ceramic surface, (x) a bandage, (xi) a surgical implant, (xii) a catheter, (xiii) tile grout, or (ix) human skin.

16. A method of forming a coating on a substrate comprising the steps of:

(a) contacting a substrate with a first solution, wherein the first solution consisting of phenolic compound comprising phenolic molecules in a first solvent; and (b) contacting the substrate with a second solution before the first solution dries on the substrate, wherein (i) the second solution comprises a low-valent metallic salt dissolved in a second solvent, (ii) the low-valent metallic salt comprises metal ions that chelate to link the phenolic molecules, and less than 50% of the phenolic molecules are covalently polymerized during the coating process, and (iii) the phenolic molecules create a coating disposed on the substrate.

17. The method of forming a coating of claim 16, wherein:

(a) the first solution is stored in a first vessel, and the first vessel is coupled to a first sprayer, and (b) the second solution is stored in a second vessel, and the second vessel is coupled to a second sprayer.

18. The method of forming a coating of claim 17, wherein the first vessel is affixed to the second vessel.

19. The method of forming a coating of claim 16, wherein:

(a) the phenolic compound is selected from one or more of tannic acid, gallic acid, caffeic acid, resveratrol, persimmon tannin, grapeseed extract, gallnut extract, proanthocyanidins, pyrogallol, epigallocatechin gallate, pyrocatechol, or catechin; and (b) the low-valent metallic salt is selected from one or more of silver nitrate, silver chloride, copper chloride, zinc chloride, or zirconyl chloride.

20. The method of forming a coating of claim 16, wherein:

(a) the phenolic compound is present in the first solution at a concentration between 0.1 mg/mL and 50 mg/mL;

(b) and (c) the low-valent metallic salt is present in the second solution at a concentration between 0.01 mg/mL and 50 mg/mL.

21. The method of forming a coating of claim 16, wherein:

(a) the step of contacting the substrate with the first solution comprises spraying the first solution on the substrate with a first spray volume between 1 μL to 10 mL per square centimeter of the substrate;

(b) the step of contacting the substrate with the second solution comprises spraying the second solution on the substrate a second spray volume between 1 μL to 10 mL per square centimeter of the substrate; and wherein (c) the method of forming a coating further comprises the step of allowing the substrate to dry for at least 60 seconds.

22. The method of forming a coating of claim 21, wherein: (a) a coating is formed on the substrate after 60 seconds; and (b) the coating is less than 200 nanometers in thickness.

23. The method of forming a coating of claim 16, wherein:

(a) the method further comprises the step of contacting the substrate with a third solution before the first solution dries on the substrate; and wherein (b) the third solution comprises a charged polymer compound in a third solvent.

24. The method of forming a coating of claim 16, wherein:

(a) the method further comprises the step of contacting the substrate with a third solution; and wherein (b) the third solution comprises an antimicrobial organic compound in a third solvent.

25. The method of forming a coating of claim 24, wherein the antimicrobial organic compound is selected from one or more of an antibiotic, a quaternary ammonium compound, or an azole.

\* \* \* \* \*